US012564307B2

(12) United States Patent
Demura

(10) Patent No.: US 12,564,307 B2
(45) Date of Patent: Mar. 3, 2026

(54) IMAGE ANALYSIS PROCESSING APPARATUS, ENDOSCOPE SYSTEM, OPERATION METHOD OF IMAGE ANALYSIS PROCESSING APPARATUS, AND NON-TRANSITORY COMPUTER READABLE MEDIUM

(71) Applicant: FUJIFILM Corporation, Tokyo (JP)

(72) Inventor: Takanori Demura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 395 days.

(21) Appl. No.: 18/153,136

(22) Filed: Jan. 11, 2023

(65) Prior Publication Data

US 2023/0141302 A1 May 11, 2023

Related U.S. Application Data

(63) Continuation of application No. PCT/JP2021/022684, filed on Jun. 15, 2021.

(30) Foreign Application Priority Data

Jul. 14, 2020 (JP) ................................. 2020-120459

(51) Int. Cl.
*A61B 1/00* (2006.01)
*A61B 1/06* (2006.01)
*G06T 7/00* (2017.01)

(52) U.S. Cl.
CPC ...... *A61B 1/00045* (2013.01); *A61B 1/00006* (2013.01); *A61B 1/0638* (2013.01);
(Continued)

(58) Field of Classification Search
CPC ..................... G06T 7/0012; G06T 5/00; G06T 2207/10068; G06T 2207/10152;
(Continued)

(56) References Cited

U.S. PATENT DOCUMENTS 10,127,665 B1 11/2018 Ding et al.
2016/0331224 A1 11/2016 Uji et al.
(Continued)

FOREIGN PATENT DOCUMENTS

CN 106157297 A 11/2016
CN 107220975 A 9/2017
(Continued)

OTHER PUBLICATIONS

An Office Action; "Notice of Reasons for Refusal," mailed by the Japanese Patent Office on Jan. 16, 2024, which corresponds to Japanese Patent Application No. 2022-536182 and is related to U.S. Appl. No. 18/153,136; with English language translation.
(Continued)

*Primary Examiner* — Matthew C Bella
*Assistant Examiner* — Daniel Joseph Santos
(74) *Attorney, Agent, or Firm* — Studebaker Brackett PLLC

(57) ABSTRACT

There is provided an image analysis processing apparatus including a processor, in which the processor acquires a plurality of types of analysis images used in image analysis, performs the image analysis on the analysis image in parallel for each type of analysis image, acquires a plurality of analysis results through the image analysis, and performs control of displaying, on a display, an analysis result display based on the plurality of analysis results and a display image based on at least one type of analysis image among the plurality of types of analysis images.

20 Claims, 21 Drawing Sheets

(52) U.S. Cl.
CPC .. *G06T 7/0012* (2013.01); *G06T 2207/10068* (2013.01); *G06T 2207/10152* (2013.01); *G06T 2207/30032* (2013.01); *G06T 2207/30096* (2013.01); *G06T 2207/30101* (2013.01)

(58) Field of Classification Search
CPC . G06T 2207/30032; G06T 2207/30096; G06T 2207/30101; A61B 1/00006; A61B 1/00045; A61B 1/0638; A61B 1/000094; A61B 1/000096; A61B 1/0005; A61B 1/0655; A61B 1/045; A61B 1/063; A61B 1/00009; A61B 1/00; A61B 1/000095; A61B 1/043
USPC ........................................................ 382/128
See application file for complete search history.

(56) References Cited

U.S. PATENT DOCUMENTS

| | | | | |
|---|---|---|---|---|
| 2019/0073768 A1 * | 3/2019 | Shigeta | ................. | G06T 7/0012 |
| 2020/0022560 A1 * | 1/2020 | Oosake | ............. | A61B 1/00009 |
| 2020/0143538 A1 * | 5/2020 | Kamon | ................. | G06T 7/0012 |
| 2020/0184645 A1 * | 6/2020 | Kamon | ................. | G06T 7/0012 |
| 2020/0337537 A1 | 10/2020 | Hirasawa et al. | | |
| 2020/0383553 A1 | 12/2020 | Kamon | | |
| 2023/0222654 A1 * | 7/2023 | Fan et al. | ............. | G06T 7/0012 |

FOREIGN PATENT DOCUMENTS

| | | | | |
|---|---|---|---|---|
| EP | 3 811 845 A1 | 4/2021 | | |
| JP | WO2019087971 A1 * | 5/2019 | ............... | A61B 1/00 |
| JP | WO2019167623 A1 * | 9/2019 | ............ | A61B 1/045 |
| JP | 6657480 B2 | 3/2020 | | |
| JP | 2020-065685 A | 4/2020 | | |
| TW | 201922174 A | 6/2019 | | |
| WO | 2019/167623 A1 | 9/2019 | | |
| WO | 2019/245009 A1 | 12/2019 | | |

OTHER PUBLICATIONS

International Search Report issued in PCT/JP2021/022684; mailed Sep. 7, 2021.
International Preliminary Report On Patentability (Chapter I) and Written Opinion of the International Searching Authority issued in PCT/JP2021/022684; issued Jan. 17, 2023.
The extended European search report issued by the European Patent Office on Nov. 7, 2023, which corresponds to European Patent Application No. 21842709.4-1126 and is related to U.S. Appl. No. 18/153,136.
An Office Action mailed by China National Intellectual Property Administration on Jul. 10, 2025, which corresponds to Chinese Patent Application No. 202180061060.2 and is related to U.S. Appl. No. 18/153,136; with English language translation.
An Office Action mailed by China National Intellectual Property Administration on Sep. 23, 2025, which corresponds to Chinese Patent Application No. 202180061060.2 and is related to U.S. Appl. No. 18/153,136; with English language translation.

* cited by examiner

IMAGE ANALYSIS PROCESSING UNIT    ~63

FIRST IMAGE ANALYSIS UNIT    ~71

SECOND IMAGE ANALYSIS UNIT    ~72

THIRD IMAGE ANALYSIS UNIT    ~73 nTH IMAGE ANALYSIS UNIT    ~74

ANALYSIS IMAGE → ASSOCIATION INFORMATION ACQUISITION UNIT → SPECIFIC STATE (REGION AND DETAILS)

FIG. 24

SUSPECTED CANCER
PROBABILITY: 50%

NORMAL LIGHT

SPECIAL LIGHT
DETECTION
ACCURACY: 80%

85
82
18
89
95

IMAGE ANALYSIS PROCESSING APPARATUS, ENDOSCOPE SYSTEM, OPERATION METHOD OF IMAGE ANALYSIS PROCESSING APPARATUS, AND NON-TRANSITORY COMPUTER READABLE MEDIUM

CROSS-REFERENCE TO RELATED APPLICATIONS

This application is a Continuation of PCT International Application No. PCT/JP2021/022684 filed on 15 Jun. 2021, which claims priority under 35 U.S.C § 119(a) to Japanese Patent Application No. 2020-120459 filed on 14 Jul. 2020. The above application is hereby expressly incorporated by reference, in its entirety, into the present application.

BACKGROUND OF THE INVENTION

1. Field of the Invention

The present invention relates to an image analysis processing apparatus, an endoscope system, an operation method of an image analysis processing apparatus, and a non-transitory computer readable medium.

2. Description of the Related Art

In the medical field, diagnosis using an endoscope system that comprises a light source device, an endoscope, and a processor device is widely performed. In diagnosis using the endoscope system, using an image (hereinafter, referred to as an endoscope image) obtained by imaging an observation target with the endoscope through a method called an image enhanced endoscope or image enhanced endoscopy (IEE), a surface structure, a lesion, biological information, or the like of the observation target is enhanced and displayed, and diagnostic support information for a doctor diagnosing the observation target is obtained.

A method of obtaining various types of endoscope images, a method of using an endoscope image obtained by picking up an image of an observation target and performing digital image processing thereon, a method of using an endoscope image obtained by illuminating an observation target with specific illumination light and picking up an image of the observation target, or the like is known as IEE. For example, as a doctor selects a specific type of endoscope image, biological information, such as a region of the observation target in which blood vessels are dense and a region where oxygen saturation is low, is determined, and the regions are enhanced and displayed on the display or the like. Such a display is useful as diagnostic support information for the doctor to diagnose the observation target.

In addition, computer-aided diagnosis (CAD) technology, in which a disease stage or the like is determined from a range of a region having a probability of being a lesion in an observation target, a degree of inflammation, or the like by performing image analysis on various types of endoscope images through IEE or the like and the obtained determination results are displayed and provided on the display as diagnostic support information, has also been developed. For example, an endoscope system that determines the severity or degree of progression of a disease, such as the stage of ulcerative colitis, with high accuracy using an endoscope image obtained through IEE is known (JP2020-65685A).

SUMMARY OF THE INVENTION

In IEE, CAD, or the like, in accordance with an instruction from a doctor who is a user of the endoscope, a specific type of endoscope image is displayed on the display, and image analysis results are obtained through image analysis of the endoscope image displayed on the display so as to be used as diagnostic support information. For example, in a case where the doctor desires to observe an observation target in a bright and natural color, an endoscope image obtained by picking up an image of the observation target with illumination light as white light is displayed on the display, image analysis is performed using the endoscope image, and diagnostic support information based on image analysis results is obtained. On the other hand, in a case where the doctor desires to observe a lesion where superficial blood vessels are dense, which is the observation target, in detail, brightness is inferior compared to the endoscope image based on white light, an endoscope image in which superficial blood vessels are enhanced through IEE is displayed on the display, image analysis is performed using the endoscope image, and diagnostic support information based on image analysis results is obtained.

As described above, since effects, objects, or applications to be obtained depending on the type of endoscope image obtained through IEE or CAD are different, there can be diagnostic support information that is not necessarily well obtained in image analysis of the type of endoscope image displayed on the display in accordance with a doctor's instruction or the like. On the other hand, in a different type of endoscope image, the diagnostic support information is well obtained in some cases. Therefore, in a case of using IEE or CAD in observation through the endoscope, for example, although there is diagnostic support information well obtained in image analysis using a different type of endoscope image, the diagnostic support information is not well obtained even in a case where the same image analysis is performed depending on the type of endoscope image. Thus, there is a probability that an abnormality of an observation target such as a lesion is overlooked.

An object of the present invention is to provide an image analysis processing apparatus, an endoscope system, an operation method of an image analysis processing apparatus, and a non-transitory computer readable medium that prevent a region-of-interest in an endoscope image from being overlooked.

The present invention is an image analysis processing apparatus that performs image analysis based on an image obtained by picking up an image of an observation target using an endoscope and comprises a processor. The processor is configured to acquire a plurality of types of analysis images used in image analysis, perform the image analysis of the analysis image in parallel for each type of the analysis image, acquire a plurality of analysis results through the image analysis, and perform control of displaying, on a display, an analysis result display based on the plurality of analysis results and a display image based on at least one type of the analysis image among the plurality of types of analysis images.

It is preferable that the processor is configured to perform the image analysis independently for each type of the analysis image.

It is preferable that the processor is configured to acquire association information in which a specific state of the observation target and the analysis image obtained by picking up an image of the observation target including the specific state are associated with each other in advance and obtain the analysis result based on the analysis image and the association information.

It is preferable that the processor is configured to acquire the association information for each type of the analysis image and obtain the analysis result based on the analysis image and the association information acquired corresponding to the type of the analysis image.

It is preferable that the specific state is at least one of a state where a structure of the observation target is abnormal, a state where the observation target is a specific lesion, or a state where a value of biological information of the observation target is abnormal.

It is preferable that the analysis result includes information of a region of the specific state of the observation target.

It is preferable that the analysis result includes accuracy related to the analysis result.

It is preferable that the processor is configured to select the analysis result having highest accuracy related to the analysis result as an analysis result-of-interest by comparing the plurality of analysis results with each other and create the analysis result display including the analysis result-of-interest.

It is preferable that the processor is configured to generate a first analysis image by performing an enhancement process on the image and acquire the first analysis image as one type of the analysis image.

It is preferable that the processor is configured to perform a color enhancement process or a structure enhancement process on the image.

It is preferable that the processor is configured to acquire the analysis result in association with the type of the analysis image from which the analysis result is obtained and perform control of displaying, on the display, a legend display showing association between the analysis result and the type of the analysis image from which the analysis result is obtained.

In addition, the present invention is an endoscope system comprising the image analysis processing apparatus and a light source unit that emits illumination light with which the observation target is irradiated.

It is preferable that the processor is configured to acquire the image obtained by picking up an image of the observation target illuminated with each of a plurality of rays of illumination light emitted by the light source unit, which have optical spectra different from each other, as each of different types of the analysis images from each other.

It is preferable that the processor is configured to acquire the image obtained by picking up an image of the observation target illuminated with white illumination light emitted by the light source unit as one type of the analysis image.

It is preferable that the processor is configured to acquire the image obtained by picking up an image of the observation target illuminated with illumination light, which is emitted by the light source unit and includes narrowband light in a wavelength range set in advance, as one type of the analysis image.

It is preferable that the light source unit repeatedly emits each of a plurality of rays of illumination light having optical spectra different from each other in order set in advance.

It is preferable that the processor is configured to acquire the analysis result in association with the type of the analysis image from which the analysis result is obtained and perform control of displaying, on the display, a legend display showing association between the analysis result and the type of the analysis image from which the analysis result is obtained.

In addition, the present invention is an operation method of an image analysis processing apparatus that performs image analysis based on an image obtained by picking up an image of an observation target using an endoscope, the operation method comprising an analysis image acquisition step of acquiring a plurality of types of analysis images used in image analysis, an image analysis processing step of performing the image analysis on the analysis image in parallel for each type of the analysis image, an analysis result acquisition step of acquiring a plurality of analysis results through the image analysis, and a display control step of performing control of displaying, on a display, a display image including an analysis result display based on the plurality of analysis results and at least one type of the analysis image among the plurality of types of analysis images.

In addition, the present invention is a non-transitory computer readable medium for performing image analysis based on an image obtained by picking up an image of an observation target using an endoscope, the computer-executable program causing a computer to execute an analysis image acquisition function of acquiring a plurality of types of analysis images used in image analysis, an image analysis processing function of performing the image analysis on the analysis image in parallel for each type of the analysis image, an analysis result acquisition function of acquiring a plurality of analysis results through the image analysis, and a display control function of performing control of displaying, on a display, a display image including an analysis result display based on the plurality of analysis results and at least one type of the analysis image among the plurality of types of analysis images.

With the present invention, a region-of-interest in an endoscope image can be prevented from being overlooked.

BRIEF DESCRIPTION OF THE DRAWINGS

FIG. 24 is an image view for describing a display image displaying, in text, an analysis result display based on the image which is not displayed.

DESCRIPTION OF THE PREFERRED EMBODIMENTS

Figure 1:
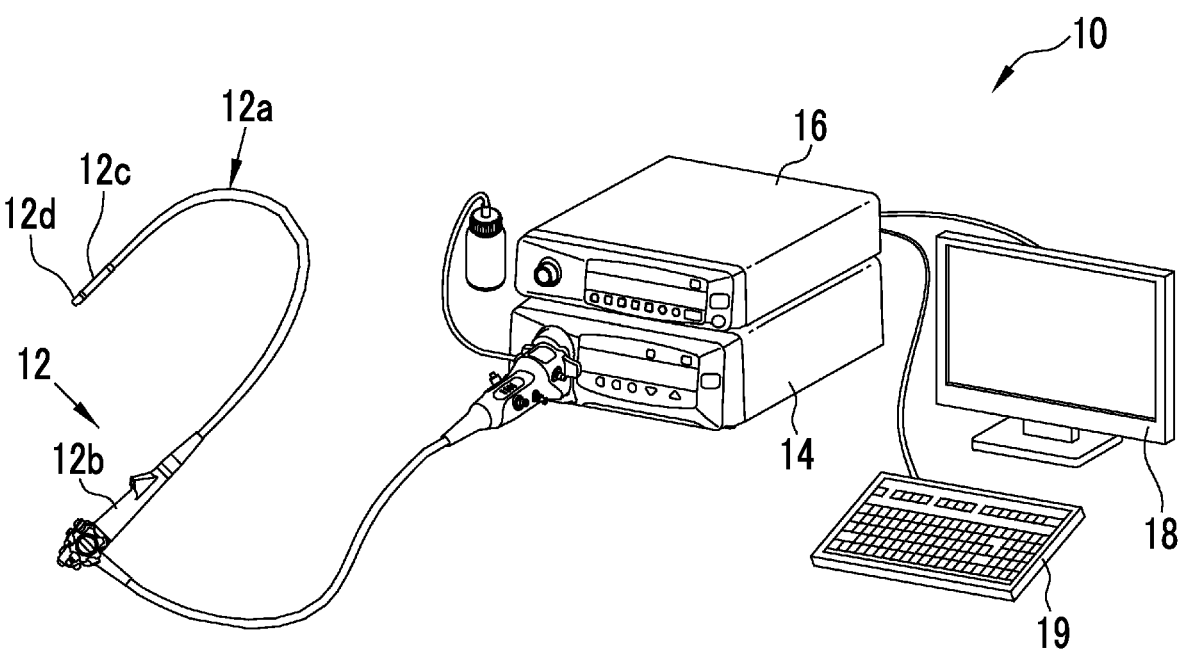
FIG. 1 is an external view of an endoscope system.

As shown in FIG. 1, an endoscope system 10 comprises an endoscope 12, a light source device 14, a processor device 16, a display 18, and a keyboard 19. The endoscope 12 images an observation target. The light source device 14 emits illumination light with which the observation target is irradiated. The processor device 16 is an image analysis processing apparatus and performs system control of the endoscope system 10, an image analysis process of an endoscope image, or the like. The display 18 is a display unit that displays a display image including an endoscope image. The keyboard 19 is an input device that performs setting input or the like into the processor device 16 or the like.

The endoscope system 10 includes, as observation modes, three modes including a normal mode, a special mode, and an image analysis mode. In the normal mode, by irradiating an observation target with normal light and picking up an image of the observation target, a normal light image having a natural hue is displayed on the display 18 as a display image. In the special mode, by illuminating an observation target with normal light and special light having a different wavelength range or a different optical spectrum and picking up an image of the observation target, a special light image, in which a specific structure or the like of the observation target is enhanced, is displayed on the display 18 as a display image. In the image analysis mode, a plurality of analysis results are obtained by performing image analysis on a plurality of types of analysis images based on a normal light image, a special light image, or the like in a case of displaying the normal light image or the special light image, which is obtained by irradiating an observation target with normal light or special light and picking up an image of the observation target, on the display 18. Then, a display image obtained by superimposing an analysis result display based on the plurality of analysis results on an observation image including the normal light image, the special light image, or the like is displayed on the display 18. In the normal mode or the image analysis mode, insofar as an image has good visibility, even an enhanced image on which an enhancement process or the like is performed may be used in display as a normal light image or a special light image.

The type of analysis image used in image analysis is classified by the type of illumination light and the type of enhancement process. Therefore, an endoscope image having the same illumination light is the same type of analysis image, and an endoscope image having different illumination light is a different type of analysis image. In addition, an endoscope image on which an enhancement process is performed through the same method is the same type of analysis image, and an endoscope image on which an enhancement process is performed through a different method is a different type of analysis image. The type of illumination light is classified by an optical spectrum of illumination light. In a case where illumination light is different, an optical spectrum of illumination light is different. Therefore, for example, an endoscope image picked up with white light and an endoscope image picked up with illumination light other than white light are different types of analysis images. In addition, the type of enhancement process is classified by a method of an enhancement process. Therefore, for example, an endoscope image which is picked up with white light and on which a color enhancement process is performed and an endoscope image which is picked up with white light and on which a structure enhancement process is performed are different types of analysis images.

Figure 2:
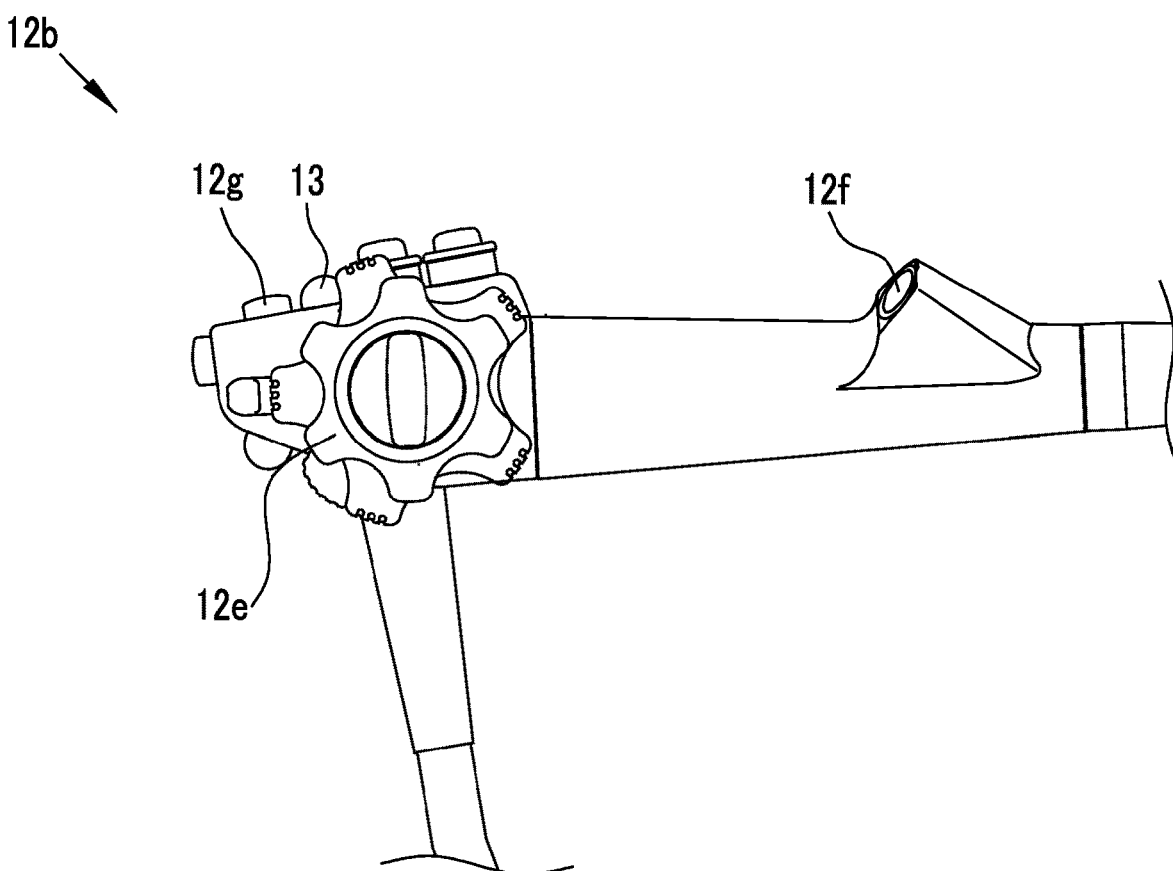
FIG. 2 is an external view of an operating part of an endoscope.

The endoscope 12 has an insertion part 12a inserted into a subject having an observation target, an operating part 12b provided at a proximal end portion of the insertion part 12a, a bendable part 12c provided at a distal end side of the insertion part 12a, and a distal end part 12d. The bendable part 12c bends by operating an angle knob 12e (see FIG. 2) of the operating part 12b. As a result, the distal end part 12d is directed in a desired direction. In addition, as shown in FIG. 2, at the operating part 12b, a treatment tool insertion port 12f, a scope button 12g, and a zoom operation part 13 are provided, in addition to the angle knob 12e. The treatment tool insertion port 12f is an entrance into which a treatment tool such as biopsy forceps, a snare, and an electric scalpel is inserted. A treatment tool inserted into the treatment tool insertion port 12f protrudes from the distal end part 12d. Various types of operations can be assigned to the scope button 12g, and the scope button 12g is used in an operation of switching observation modes in the present embodiment. By operating the zoom operation part 13, an observation target can be imaged while magnified or reduced.

Figure 3:
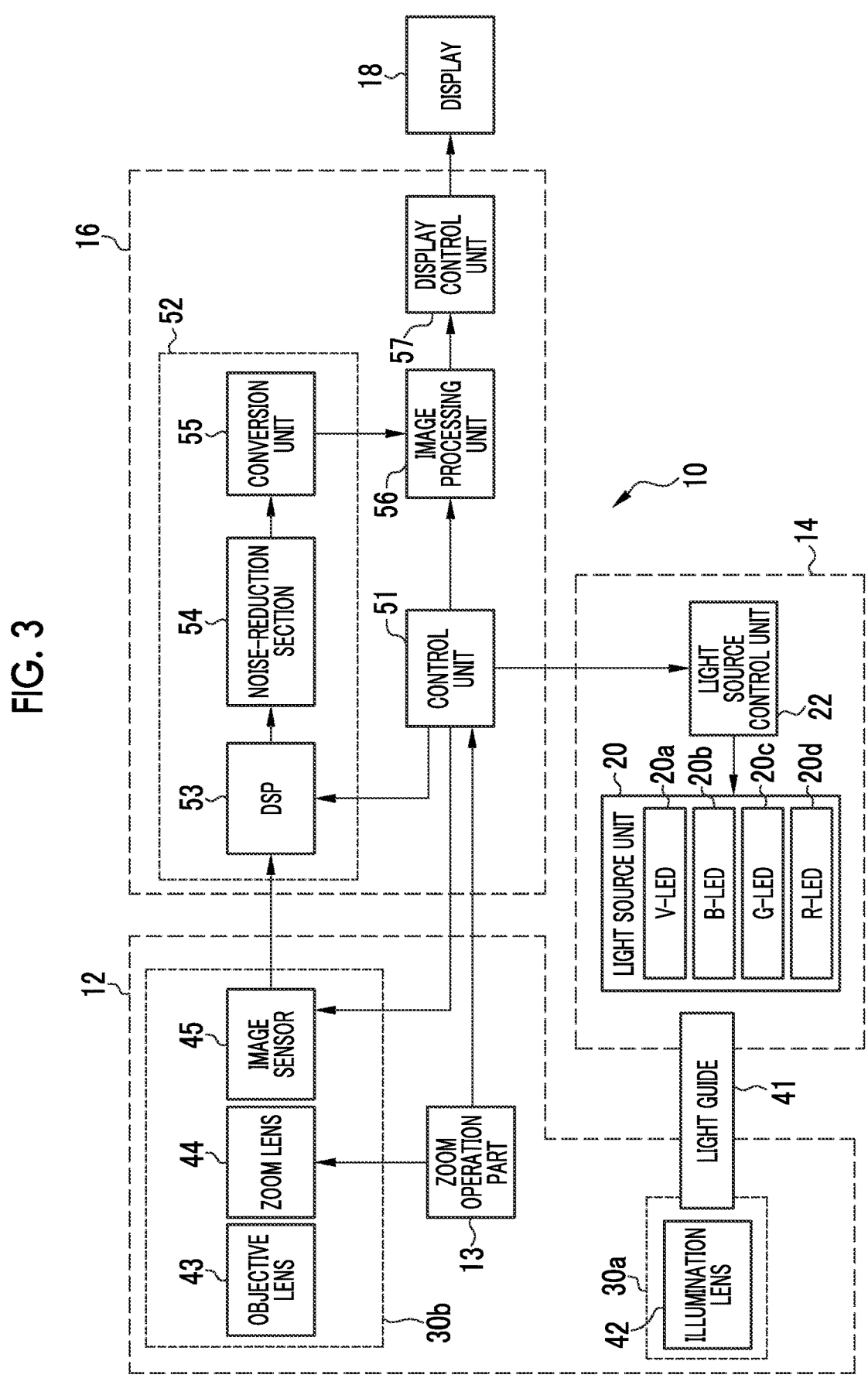
FIG. 3 is a block diagram showing a function of the endoscope system.

As shown in FIG. 3, the light source device 14 comprises a light source unit 20 that comprises a light source which emits illumination light and a light source control unit 22 that controls an operation of the light source unit 20. The light source unit 20 emits illumination light that illuminates an observation target. The illumination light includes emission of light such as excitation light used in order to emit illumination light. The light source unit 20 includes a light source such as a laser diode, a light emitting diode (LED), a xenon lamp, and a halogen lamp and emits at least white illumination light or excitation light used in order to emit white illumination light. The color of white includes a so called color of pseudo-white that is substantially equivalent to white in imaging of an observation target using the endoscope 12.

The light source unit 20 includes, as necessary, a phosphor that emits light by being irradiated with excitation light or an optical filter that adjusts a wavelength range, an optical spectrum, or a light amount of illumination light or excitation light. In addition, the light source unit 20 can emit illumination light consisting of at least light with a narrowband (hereinafter, referred to as narrowband light). In addition, the light source unit 20 can emit a plurality of rays of illumination light having optical spectra different from each other. The illumination light may include narrowband light. In addition, the light source unit 20 can emit, for example, light having a specific wavelength range or a specific optical spectrum, which is necessary in capturing an image used in order to calculate biological information such as oxygen saturation of hemoglobin included in an observation target.

The "narrowband" refers to a substantially almost single wavelength range in a relationship of characteristics of an observation target and/or spectral characteristics of a color filter included in an image sensor 45. For example, in a case where a wavelength range is, for example, approximately ±20 nm or lower (preferably approximately ±10 nm or lower), the light is narrowband light.

In the present embodiment, the light source unit 20 has four colors of LEDs including a V-LED 20a, a B-LED 20b, a G-LED 20c, and an R-LED 20d. The V-LED 20a emits violet light VL having a central wavelength of 405 nm and a wavelength range of 380 to 420 nm. The B-LED 20b emits blue light BL having a central wavelength of 460 nm and a wavelength range of 420 to 500 nm. The G-LED 20c emits green light GL having a wavelength range of 480 to 600 nm. The R-LED 20d emits red light RL having a central wavelength of 620 to 630 nm and a wavelength range of 600 to 650 nm. The central wavelengths of the V-LED 20a and the B-LED 20b have a range of approximately ±20 nm, preferably approximately ±5 nm to approximately ±10 nm. The violet light VL is light having a small wavelength used in order to detect concentration of superficial blood vessels, intramucosal bleeding, and extramucosal bleeding used in the special mode or the image analysis mode and is preferable to include 410 nm in a central wavelength or a peak wavelength. In addition, it is preferable that the violet light VL is narrowband light.

The light source control unit 22 controls turning on or off of each of light sources configuring the light source unit 20, a timing of shielding, a light emission amount, and the like. As a result, the light source unit 20 can emit a plurality of types of illumination light having different optical spectra in a period set in advance and by a light emission amount set in advance. In the present embodiment, the light source control unit 22 adjusts an optical spectrum of illumination light by inputting each independent control signal for turning on and off of each of the LEDs 20a to 20d, a light emission amount in a case of turning on, insertion or removal of an optical filter, or the like. Accordingly, the light source unit 20 emits white illumination light, a plurality of types of illumination light having different optical spectra, illumination light consisting of at least narrowband light, or the like. Endoscope images obtained by picking up images of an observation target illuminated with a plurality of rays of illumination light respectively having optical spectra different from each other, including illumination light, which is white light, are different types of analysis images.

Figure 4:
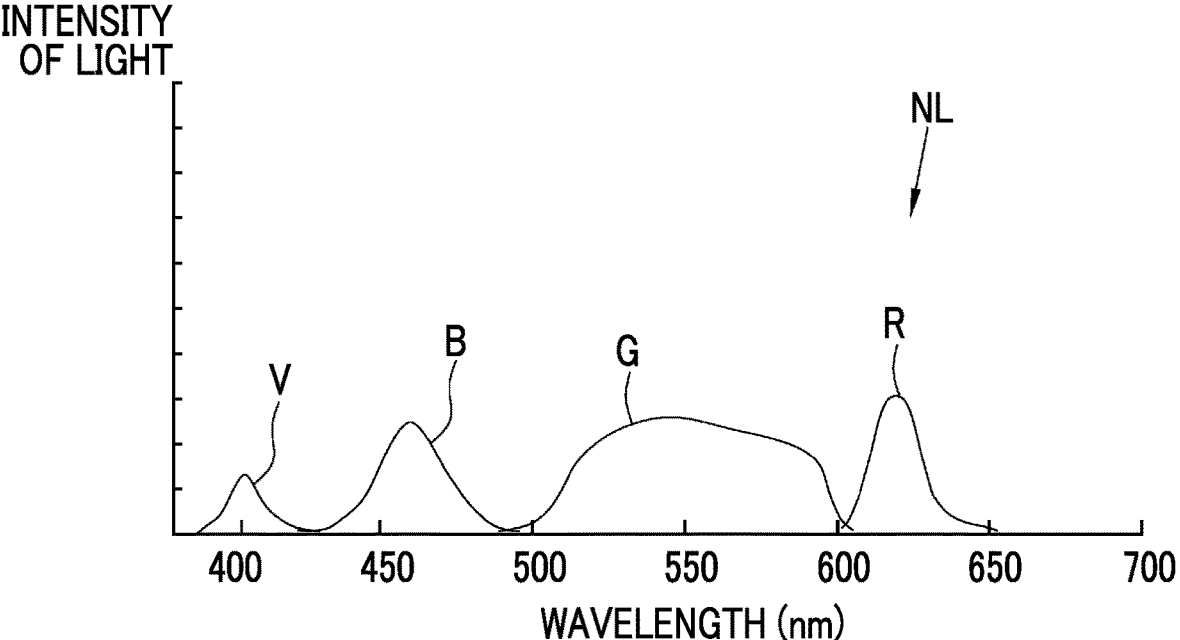
FIG. 4 is a graph showing a spectrum of normal light.

In the present embodiment, as shown in FIG. 4, the light source unit 20 emits white illumination light as normal light NL through control of the light source control unit 22. In a case where the normal mode or the image analysis mode is set, the light source control unit 22 controls each of the LEDs 20a to 20d such that white light having a ratio of intensity of light between the violet light VL, the blue light BL, the green light GL, and the red light RL of Vc:Bc:Gc:Rc is emitted. The ratio of intensity of light of Vc:Bc:Gc:Rc corresponds to a light amount condition of white illumination light. A normal light image obtained by picking up an image of an observation target illuminated with white illumination light emitted by the light source unit 20 is one type of analysis image.

Figure 5:
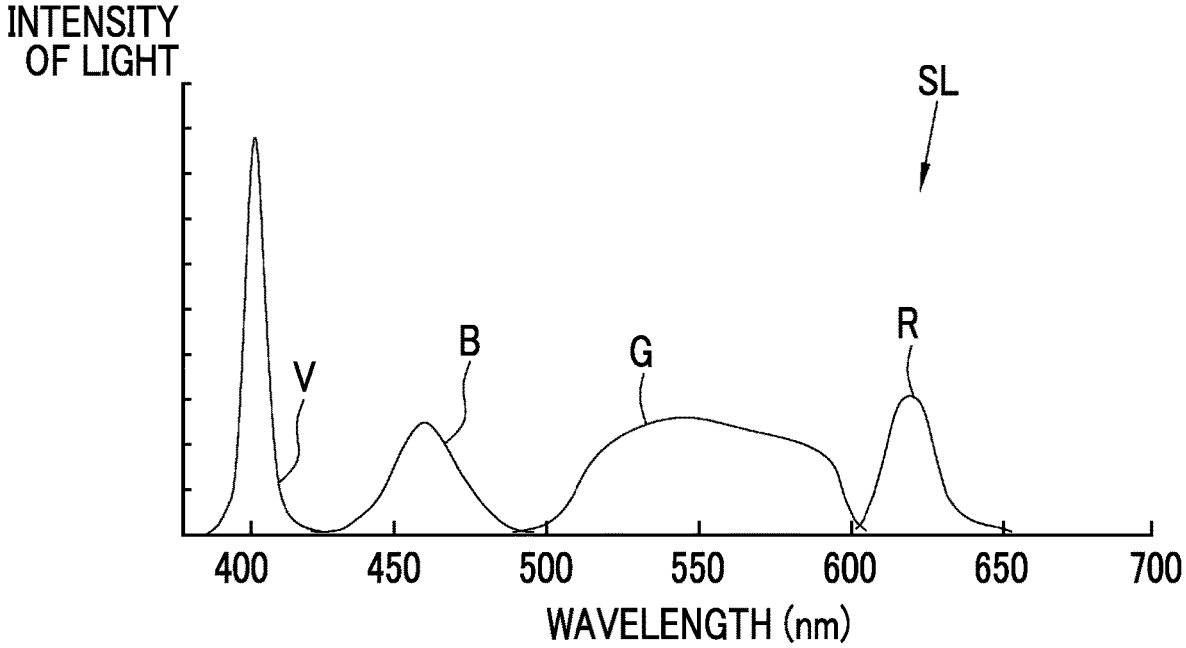
FIG. 5 is a graph showing a spectrum of special light.

In a case where the special mode or the image analysis mode is set, the light source control unit 22 controls each of the LEDs 20a to 20d such that special light having a ratio of intensity of light between the violet light VL, the blue light BL, the green light GL, and the red light RL of Vs1:Bs1:Gs1:Rs1 is emitted as special light. The ratio of intensity of light of Vs1:Bs1:Gs1:Rs1 corresponds to a light amount condition of special light. It is preferable that special light enhances structures of a superficial blood vessel, a polyp, and the like. For this reason, it is preferable to make special light such that the intensity of the violet light VL is higher than the intensity of the blue light BL. For example, as shown in FIG. 5, a ratio between light intensity Vs1 of the violet light VL and light intensity Bs1 of the blue light BL is "4:1". Special light SL of the present embodiment is illumination light including the violet light VL which is narrowband light. A special light image obtained by picking up an image of an observation target illuminated with the special light SL emitted by the light source unit 20 is one type of analysis image.

In the present specification, a case where a ratio of intensity of light is such that a ratio of at least one semiconductor light source is 0 (zero) is included. Therefore, a case where any one or two or more of semiconductor light sources are not turned on is included. For example, as in a case where a ratio of intensity of light between the violet light VL, the blue light BL, the green light GL, and the red light RL is 1:0:0:0, also a case where only one semiconductor light source is turned on and other three semiconductor light sources are not turned on has a ratio of intensity of light.

Figure 6:
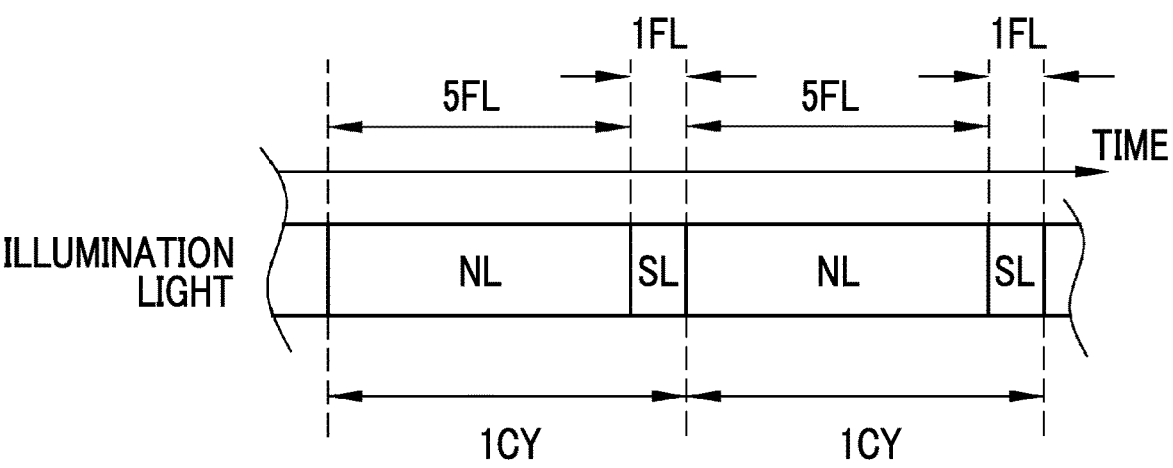
FIG. 6 is an explanatory view for describing an illumination light pattern.

It is preferable that the light source unit 20 repeatedly emits each of a plurality of rays of illumination light having optical spectra different from each other in order set in advance. In the present embodiment, the normal light NL and the special light SL are repeatedly emitted in the order set in advance. In the present embodiment, the light source control unit 22 emits, for example, as shown in FIG. 6, the normal light NL for consecutively five frames (5FL), next, the special light SL for one frame (1FL), normal light NL again for consecutively five frames (5FL), and the special light SL again for one frame (1FL). An illumination pattern consisting of order in which the normal light NL is emitted for consecutively five frames (5FL) and next, the special light SL is emitted for one frame (1FL) is used as one period (1CY), and this period is repeated.

An illumination optical system 30a and an imaging optical system 30b are provided at the distal end part 12d of the endoscope 12 (see FIG. 3). The illumination optical system 30a has an illumination lens 42, and illumination light is emitted toward an observation target via the illumination lens 42.

The imaging optical system 30b has an objective lens 43, a zoom lens 44, and the image sensor 45. The image sensor 45 images an observation target using reflected light of illumination light returning from the observation target or the like (including scattered light, fluorescence emitted by the observation target, or fluorescence attributable to drug administered or the like to the observation target, or the like, in addition to the reflected light) via the objective lens 43 and the zoom lens 44. The zoom lens 44 moves as the zoom operation part 13 operates, and an observation target image is magnified or reduced.

The image sensor 45 has one color of color filter among a plurality of colors of color filters, for each pixel. In the present embodiment, the image sensor 45 is a color sensor having a primary color system color filter. Specifically, the image sensor 45 has an R pixel having a red color filter (R filter), a G pixel having a green color filter (G filter), and a B pixel having a blue color filter (B filter).

As the image sensor 45, a charge coupled device (CCD) sensor and a complementary metal oxide semiconductor (CMOS) sensor are usable. In addition, the image sensor 45 of the present embodiment is a primary color system color sensor, but a complementary color system color sensor can also be used. The complementary color system color sensor has, for example, a cyan pixel provided with a cyan color filter, a magenta pixel provided with a magenta color filter, a yellow pixel provided with a yellow color filter, and a green pixel provided with a green color filter. In a case where color conversion of complementary color-primary color is performed on an image obtained from each of the color pixels in a case of using the complementary color system color sensor, the image can be converted into an image which is the same as an image obtained with the primary color system color sensor. The same applies to a case of having one or a plurality of types of pixels having characteristics other than the above, such as a W pixel (a white pixel receiving light in almost the entire wavelength range), in the primary color system sensor or the complementary color system sensor. In addition, the image sensor 45 of the present embodiment is a color sensor, but a monochrome sensor that does not have a color filter may be used.

In the processor device 16, a program related to a process or the like performed by a control unit 51, an image acquisition unit 52, an image processing unit 56, a display control unit 57, and the like, which are to be described later, is incorporated into a memory (not shown). By operating the program with the control unit 51 composed of a processor included in the processor device 16 functioning as the image analysis processing apparatus, functions of the control unit 51, the image acquisition unit 52, the image processing unit 56, and the display control unit 57 are realized.

The control unit 51 performs overall control of the endoscope system 10 such as synchronization control of an irradiation timing of illumination light and an imaging timing. In a case of inputting various types of setting using the keyboard 19 and the like, the control unit 51 inputs the setting into each unit of the endoscope system 10, such as the light source control unit 22, the image sensor 45, and the image processing unit 56.

The image acquisition unit 52 acquires, from the image sensor 45, a captured image of an observation target using each color pixel, that is, an RAW image. In addition, the RAW image is an image (endoscope image) before performing a demosaicing process. Insofar as an image is an image before performing a demosaicing process, the RAW image includes also an image obtained by performing any process such as a noise reducing process is performed on an image acquired from the image sensor 45.

The image acquisition unit 52 comprises a digital signal processor (DSP) 53, a noise-reduction section 54, and a conversion unit 55, in order to perform various types of processes on an acquired RAW image as necessary.

The DSP 53 comprises, for example, an offset processing unit, a defect correction processing unit, a demosaicing processing unit, a linear matrix processing unit, a YC conversion processing unit, and the like (none of which are shown). The DSP 53 performs various types of processes on an RAW image using the units or an image generated using the RAW image.

The offset processing unit performs an offset process on an RAW image. The offset process is a process in which a dark current component is reduced from the RAW image, and an accurate zero level is set. The offset process is referred to as a clamping process in some cases. The defect correction processing unit performs a defect correction process on the RAW image. The defect correction process is a process of correcting or generating a pixel value of a RAW pixel corresponding to the defective pixel of the image sensor 45 in a case where the image sensor 45 includes a pixel (defective pixel) having a defect attributable to a manufacturing step or a change with time.

The demosaicing processing unit performs a demosaicing process on an RAW image having each color corresponding to each color of color filter. The demosaicing process is a process of generating a missing pixel value attributable to arrangement of color filters in the RAW image by interpolation. The linear matrix processing unit performs a linear matrix process on an endoscope image generated by assigning one or a plurality of RAW images to a channel of each color of RGB. The linear matrix process is a process for improving color reproduction of the endoscope image. A YC conversion process performed by the YC conversion processing unit is a process of converting an endoscope image generated by assigning one or a plurality of RAW images to a channel of each color of RGB into an endoscope image having a luminance channel Y, a color difference channel Cb, and a color difference channel Cr.

The noise-reduction section 54 performs a noise reducing process on an endoscope image having the luminance channel Y, the color difference channel Cb, and the color difference channel Cr, using, for example, a moving averaging method, a median filter method, or the like. The conversion unit 55 reconverts the luminance channel Y, the color difference channel Cb, and the color difference channel Cr after the noise reducing process into an endoscope image having a channel of each color of BGR again.

Figure 7:
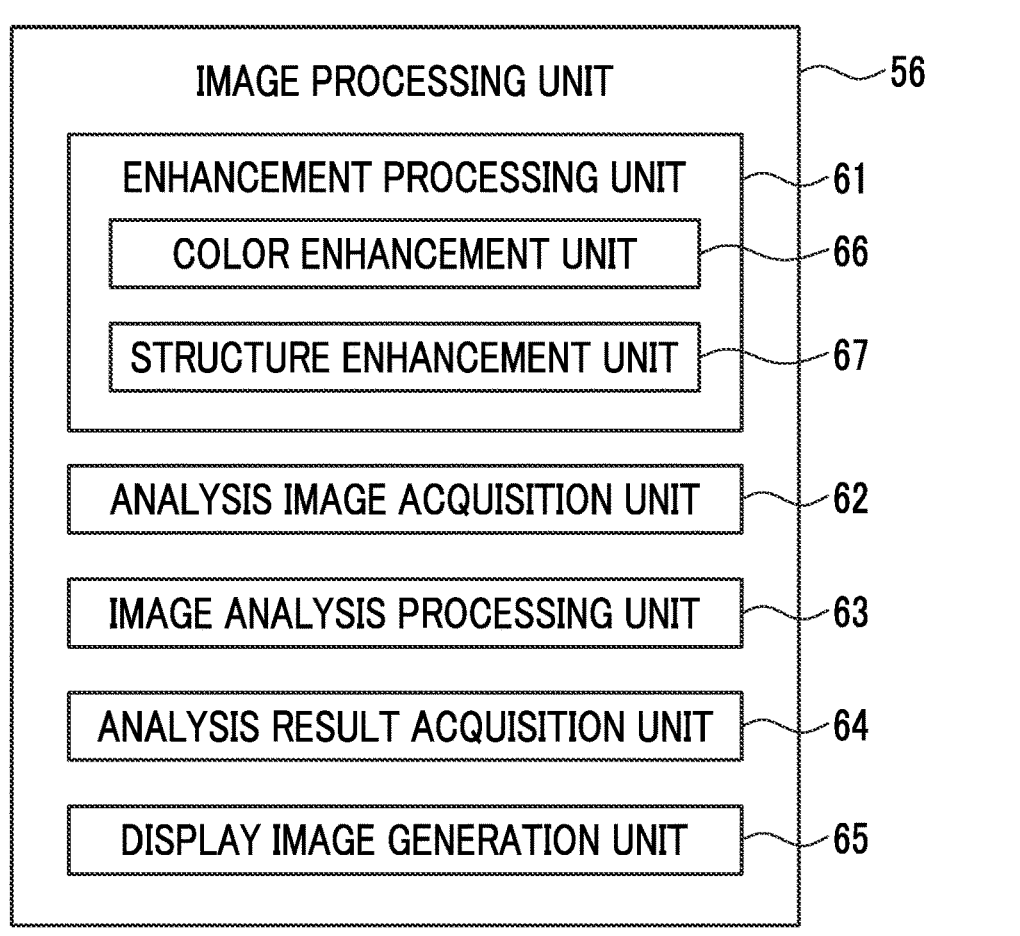
FIG. 7 is a block diagram showing a function of an image processing unit.

The image processing unit 56 performs a necessary image process, image analysis, operation, or the like on an endoscope image output by the image acquisition unit 52. As shown in FIG. 7, the image processing unit 56 comprises an enhancement processing unit 61, an analysis image acquisition unit 62, an image analysis processing unit 63, an analysis result acquisition unit 64, and a display image generation unit 65. The enhancement processing unit 61 comprises a color enhancement unit 66 and a structure enhancement unit 67.

The enhancement processing unit 61 performs an enhancement process on an endoscope image output by the image acquisition unit 52. The analysis image acquisition unit 62 acquires a plurality of types of analysis images used in image analysis. The image analysis processing unit 63 performs image analysis of an analysis image in parallel for each type of analysis image. The analysis result acquisition unit 64 acquires a plurality of analysis results through image analysis. The display image generation unit 65 generates an analysis result display and an observation image for displaying on the display 18.

An enhancement process performed by the enhancement processing unit 61 means processing on an endoscope image before an enhancement process such that information of a specific portion is obtained by distinguishing the endoscope image from other tissues, structures, or the like. For example, a process of relatively changing the color or brightness of a portion having a specific feature with respect to other portions (for example, a normal mucous membrane and the like) is an enhancement process. An endoscope image processed by the enhancement processing unit 61 may be a normal light image or a special light image. An endoscope image on which an enhancement process is performed is used as one type of analysis image.

The color enhancement unit 66 performs a color enhancement process on an acquired endoscope image to become, for example, an endoscope image in which a boundary between a normal region and an abnormal region in an observation target is clearly represented by a color and chroma saturation. The color enhancement unit 66 performs a color information conversion process on the acquired endoscope image. The color information conversion process is a process of moving each of a plurality of ranges distributed in a color space to a range, which is a conversion destination associated with a range before conversion, in the acquired endoscope image. Since the endoscope image processed by the color enhancement unit 66 has a clear boundary between a normal region and an abnormal region, the endoscope image is an image through which the abnormal region can be more easily and accurately determined as a specific region. The endoscope image on which a color enhancement process is performed is a first analysis image which is one type of analysis image.

The structure enhancement unit 67 performs a structure enhancement process on an acquired endoscope image to become, for example, an endoscope image in which a blood vessel in an observation target is enhanced and shown. The structure enhancement unit 67 acquires a shade histogram which is a graph obtained by plotting a pixel value (brightness value) on the lateral axis and a frequency on the vertical axis in the acquired endoscope image and performs gradation correction through a gradation correction table stored in advance in a memory (not shown) of the image processing unit 56 or the like. The gradation correction table has the lateral axis representing an input value and the vertical axis representing an output value, has a gradation correction curve indicating a correspondence relationship between an input value and an output value, and extends the dynamic range of an acquired endoscope image by performing gradation correction based on, for example, a substantially S-shaped gradation correction curve. Accordingly, in an original image before an enhancement process for structural enhancement, a portion having a low density has a lower density and a portion having a high density has a higher density. Thus, for example, a density difference between a blood vessel region and a region where a blood vessel does not exist increases, and contrast of blood vessels improves. Therefore, since contrast of blood vessels is improved, an endoscope image processed by the structure enhancement unit 67 has improved visibility of a blood vessel structure and is, for example, an image through which a region where a degree of density of blood vessels is high can be more easily and accurately determined as a specific region. The endoscope image on which the structure enhancement process is performed is a first analysis image, which is one type of analysis image.

The analysis image acquisition unit 62 acquires a plurality of types of analysis images. The analysis image is an image based on a normal light image or a special light image output from the image acquisition unit 52. A normal light image or a special light image, on which an enhancement process is not performed, and a normal light image or a special light image, on which an enhancement process is performed, are used as analysis images. The type of analysis image is distinguished by the type of illumination light and a method of an enhancement process. In the present embodiment, two types of analysis images including a normal light image obtained by picking up an image of an observation target illuminated with normal light and a special light image obtained by picking up an image of an observation target illuminated with special light are acquired as a plurality of types of analysis images. In the present embodiment, an enhancement process is not performed.

The image analysis processing unit 63 performs image analysis on an analysis image acquired by the analysis image acquisition unit 62 in parallel for each type of analysis image. Performing image analysis in parallel means that there are a plurality of image analysis processing units (see FIG. 8) respectively for the types of analysis images and each type of image analysis is performed. Image analysis processing for each type of analysis image may be simultaneously performed or may be performed not simultaneously. Therefore, the image analysis processing unit 63 can independently perform image analysis for each type of analysis image. In the present embodiment, each time an analysis image is acquired, image analysis is performed by a corresponding image analysis processing unit on the acquired analysis image.

Figure 8:
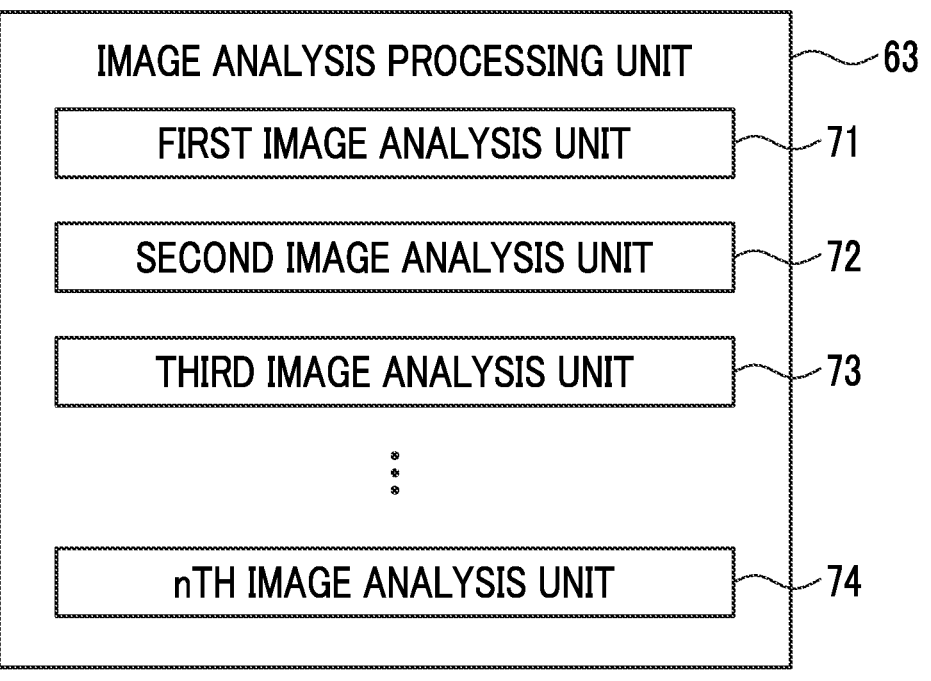
FIG. 8 is a block diagram showing a function of an image analysis processing unit.

As shown in FIG. 8, the image analysis processing unit 63 comprises a first image analysis unit 71, a second image analysis unit 72, and a third image analysis unit 73, which are provided for respective types of analysis images, and comprises each image analysis unit to an nth image analysis unit 74 corresponding to the number of types of analysis images. As described above, since the image analysis processing unit 63 comprises, for each type of analysis image, an image analysis unit corresponding to each type of analysis image and performs image analysis for each type of analysis image by each image analysis unit, image analysis is performed in parallel for each type of analysis image. In the present embodiment, the first image analysis unit 71 performs image analysis of a normal light image, the second image analysis unit 72 performs image analysis of a special light image, and the first image analysis unit 71 and the second image analysis unit 72 operate in parallel.

Image analysis can use a method of image analysis performed in the related art. In the image analysis processing unit 63, each image analysis unit from the first image analysis unit 71 to the nth image analysis unit 74 may perform image analysis of the same method, and each of the image analysis units may perform image analysis of methods different from each other according to the type of analysis image. In a case of performing image analysis of a method which is different according to the type of analysis image, it is preferable to select and perform a method of image analysis, through which good analysis results are obtained, according to the type of analysis image.

Examples of a method of image analysis include a method of using image processing, a method of using a machine learning technique, or the like. Specifically, examples of the method of image analysis include a method of using values such as a pixel value and/or a brightness value of an image, a method of calculating a value of biological information such as oxygen saturation calculated from an image and a method of using association information in which a specific state of an observation target and each analysis image obtained by picking up an image of the observation target including the specific state are associated with each other in advance. Through the methods of image analysis, the presence or absence of a lesion, a probability of being a lesion, a degree of progression or the like of a lesion, analysis result accuracy, or the like is determined.

The image analysis processing unit 63 preferably comprises an association information acquisition unit that acquires association information in which a specific state of an observation target and an analysis image obtained by picking up an image of the observation target including the specific state are associated with each other in advance. The image analysis processing unit 63 preferably obtains analysis results based on the analysis image and the association information.

A specific state of an observation target is, for example, a tint state of the observation target, a state where a structure or the like is abnormal, a state where the observation target is a specific lesion, a state where a value of biological information of an observation target is abnormal, a normal or healthy state where a lesion or the like does not exist in the observation target, or the like and is set in advance. Specifically, in a case where the observation target is the large intestine, a specific state is set as, for example, a state having an abnormality such as inflammation, redness, an ulcer, a polyp, and bleeding in the large intestine mucous membrane, a lesion such as a cancer and ulcerative colitis, or an abnormality of biological information such as having an extremely low oxygen saturation.

Figure 9:
FIG. 9 is an explanatory view for describing a function of an association information acquisition unit.

Association information is information in which in a case where an observation target is determined to be in a specific state in advance, an analysis image obtained by picking up an image of the observation target is associated with details of the specific state of the observation target, information of the region, and the like. The association information acquisition unit acquires a plurality of pieces of association information in advance. Therefore, as shown in FIG. 9, by inputting an acquired analysis image of which a specific state is unknown into the association information acquisition unit, the association information acquisition unit performs image analysis on the analysis image based on the plurality of pieces of association information and outputs a region, details, or the like related to the specific state of the observation target included in the analysis image. Outputting a region, details, or the like related to the specific state also includes content "there is no region in the specific state".

Figure 10:
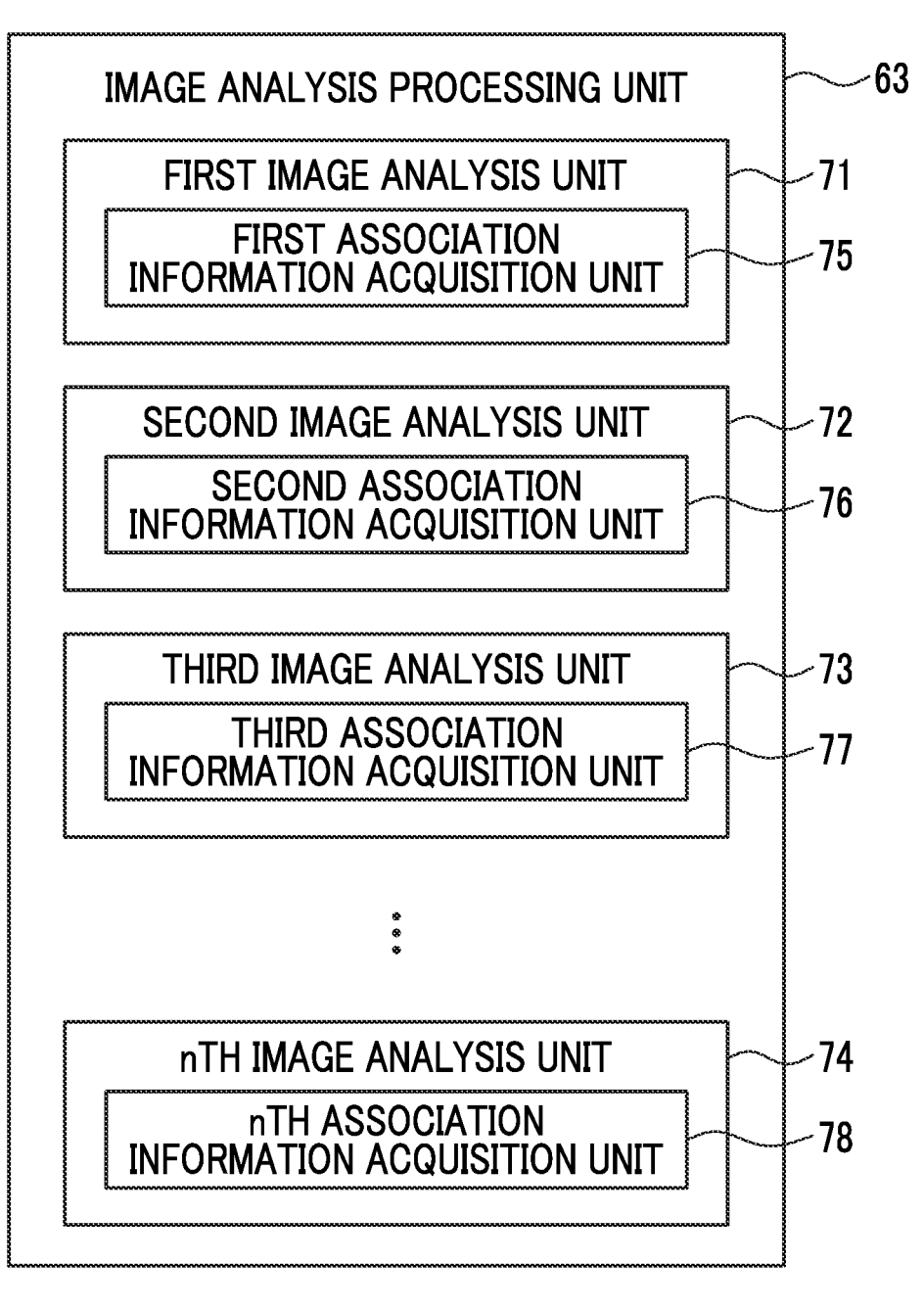
FIG. 10 is a block diagram showing the function of the image analysis processing unit comprising each association information processing unit.

The association information acquisition unit acquires association information for each type of analysis image, and the image analysis processing unit 63 preferably obtains analysis results based on an analysis image and association information acquired corresponding to the type of analysis image. The association information acquired corresponding to the type of analysis image is information in which in a case where an observation target is determined to be in a specific state in advance, a specific type of analysis image obtained by picking up an image of the observation target is associated with information such as a region, details, and the like related to the specific state of the observation target. In addition, the association information acquisition unit may perform feedback or learning to acquire analysis results after processing by the image analysis processing unit 63 as association information. As shown in FIG. 10, in the image analysis processing unit 63, the first image analysis unit 71 comprises a first association information acquisition unit 75, the second image analysis unit 72 comprises a second association information acquisition unit 76, the third image analysis unit 73 comprises a third association information acquisition unit 77, and the nth image analysis unit 74 comprises an nth association information acquisition unit 78.

A specific state of an observation target with which good results can be obtained through image analysis is different depending on the type of analysis image in some cases. Therefore, the association information acquisition unit is included for each type of analysis image. Thus, for example, in a case where the analysis image is a special light image, brightness is insufficient in image analysis, and it is difficult to detect a lesion from the special light image in a distant view, a lesion which was difficult to be detected in a distant view in the special light image can be easily detected from a normal light image, which is a different type of analysis image on which image analysis is performed in parallel. In addition, for example, since a place where blood vessels of a skin layer or a middle layer of an observation target are dense is easily detected from the special light image and a structure such as a polyp can be easily detected from the normal light image as a specific state of an observation target different from the case of the special light image, different types of regions-of-interest can be detected.

The association information acquisition unit is, for example, a trained model in machine learning. Since diagnostic support information, which is analysis results, is more quickly or accurately obtained through image analysis, it is preferable to perform image analysis using the trained model through machine learning as the association information acquisition unit. In the present embodiment, image analysis for determining the presence or absence of a lesion is performed using the trained model in machine learning as each association information acquisition unit. In this case, the trained model uses what is learned for each type of analysis image. Therefore, the first association information acquisition unit 75 and the second association information acquisition unit 76 are preferably trained models different from each other. For example, in the present embodiment, the first association information acquisition unit 75 is a trained model corresponding to a normal light image, and the second association information acquisition unit 76 is a trained model corresponding to a special light image. Each trained model may perform feedback to learn analysis results obtained by the image analysis processing unit 63.

The analysis result acquisition unit 64 acquires analysis results obtained by the image analysis processing unit 63 performing image analysis for each type of analysis image with each analysis processing unit. Since each analysis processing unit obtains each analysis result, the analysis result acquisition unit 64 acquires a plurality of analysis results. The analysis results include content corresponding to a method of performed image analysis. In the present embodiment, since a method of image analysis is determination of the presence or absence of a lesion using a trained model, analysis results are the presence or absence of a lesion in an observation target included in an analysis image on which image analysis is performed and a region in a case where there is a lesion.

In the present embodiment, two types of analysis results including a first analysis result obtained by analyzing a normal light image and a second analysis result obtained by analyzing a special light image are obtained. The first analysis result is the presence or absence of a lesion, which is a specific state of an observation target, and a region in a case where there is a lesion, which are obtained based on a normal light image. The second analysis result is the presence or absence of a lesion, which is a specific state of the same observation target, a region in a case where there is a lesion, which are obtained based on a special light image.

Figure 11:
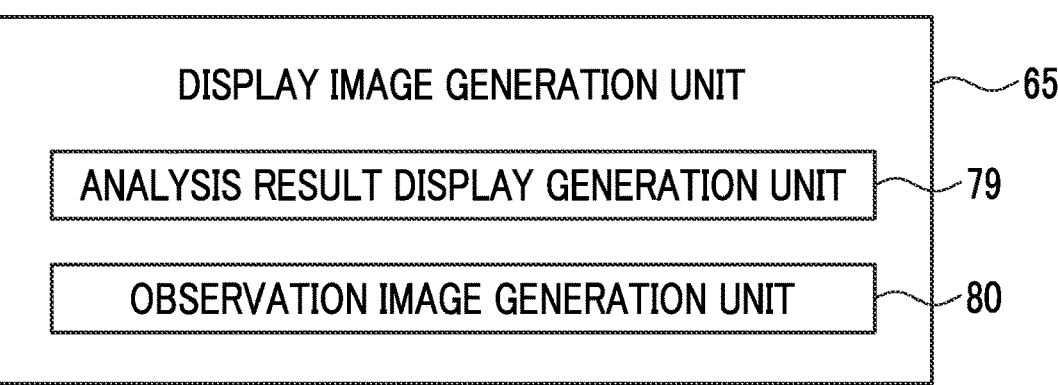
FIG. 11 is a block diagram showing a function of a display image generation unit.

As shown in FIG. 11, the display image generation unit 65 comprises an analysis result display generation unit 79 and an observation image generation unit 80. The analysis result display generation unit 79 generates an analysis result display based on a plurality of analysis results. The observation image generation unit 80 generates an observation image including an observation target based on at least one type of analysis image among a plurality of types of analysis images. The analysis result display is a display for notifying a user, such as a doctor, of a plurality of analysis results, and any display form may be adopted insofar as the display is a display through which the user can learn the plurality of analysis results. The plurality of analysis results are selected according to conditions set in advance. For example, in the present embodiment, in a case where one frame of special light image in which illumination light is the special light SL is acquired, and five frames of normal light images in which illumination light is the normal light NL are acquired consecutively. In the conditions set in advance in this case, for example, the second analysis result based on one frame of acquired special light image and the first analysis result based on a plurality of specific numbers of frames of normal light images before and after acquiring the special light image are selected as a plurality of analysis results.

The plurality of analysis results may be displayed by being distinguished from each other or may be displayed without being distinguished from each other in some cases. Specifically, for example, the plurality of analysis results may be a display by a figure, a color, a pattern, text, or a combination thereof. The size of a figure or the like is preferably adjusted to, for example, the size of a region where an observation target is in a specific state. In a case where the displays of the plurality of analysis results are shown by the same size of figures in the same region, it is preferable to adjust the size of the display of each analysis result and to display the figures such that the figures do not overlap each other. In a case where it is not necessary to display analysis results, such as a case where a specific state, such as a lesion, is not detected, the analysis results are not displayed.

In the present embodiment, two analysis results including a first analysis result and a second analysis result are acquired, and the results are distinguished and displayed. In addition, the analysis result display is a display in a form, in which analysis results are the presence or absence of a lesion, which is an observation target, and a region in a case where there is lesion and the first analysis result and the second analysis result can be distinguished.

Figure 12:
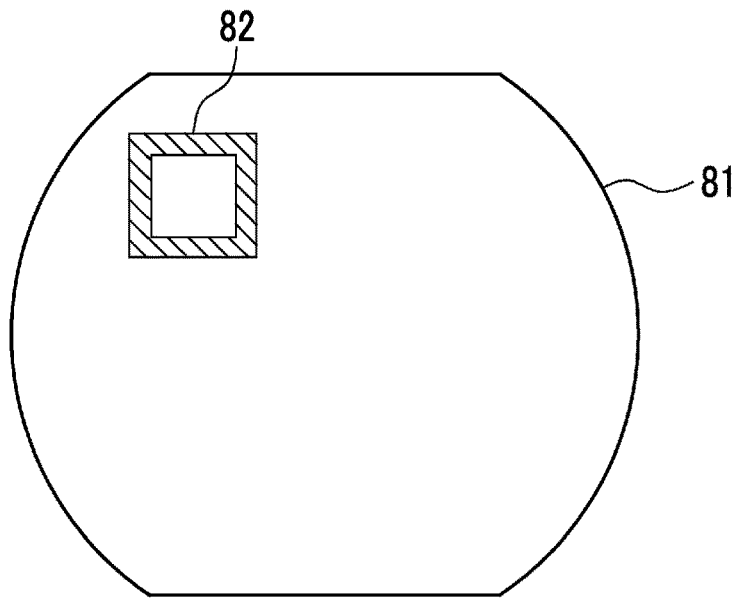
FIG. 12 is an image view for describing a first analysis result display.
Figure 13:
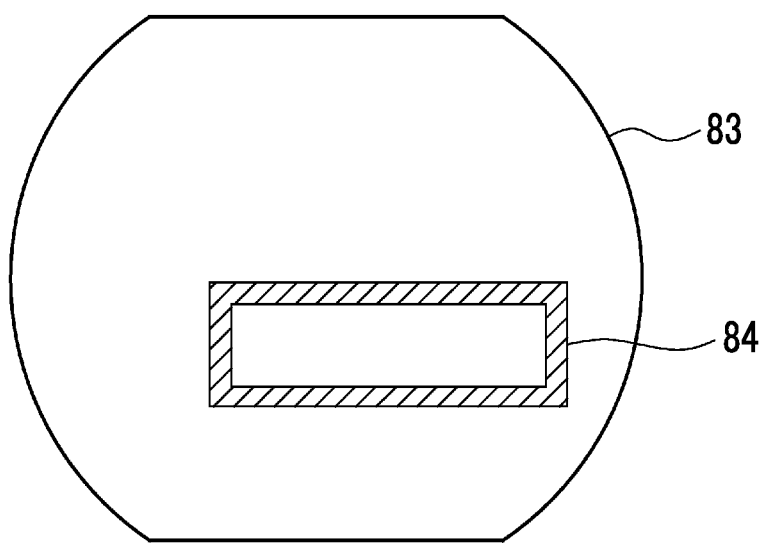
FIG. 13 is an image view for describing a second analysis result display.

In a case where a lesion is detected as a specific state of an observation target in a first analysis result and a second analysis result, as shown in FIG. 12, a first analysis result display 81 showing the first analysis result shows a region of a lesion in the observation target by surrounding with a square FIG. 82. In addition, as shown in FIG. 13, a second analysis result display 83 showing the second analysis result shows a region of a lesion in the observation target by surrounding with a square FIG. 84. The FIG. 82 and the FIG.

84 are represented by different colors. In FIGS. 11 and 12, diagonal lines in different directions indicate different colors.

The display image generation unit 65 also generates an observation image based on at least one type of analysis image among a plurality of types of analysis images. The observation image is an analysis image selected to be displayed on the display 18 by a user. The display image generation unit 65 generates an observation image by performing image processing on the analysis image selected for display in a case where it is necessary for displaying on the display 18. In the present embodiment, the observation image is continuously displayed until a display switching instruction is given.

Figure 14:
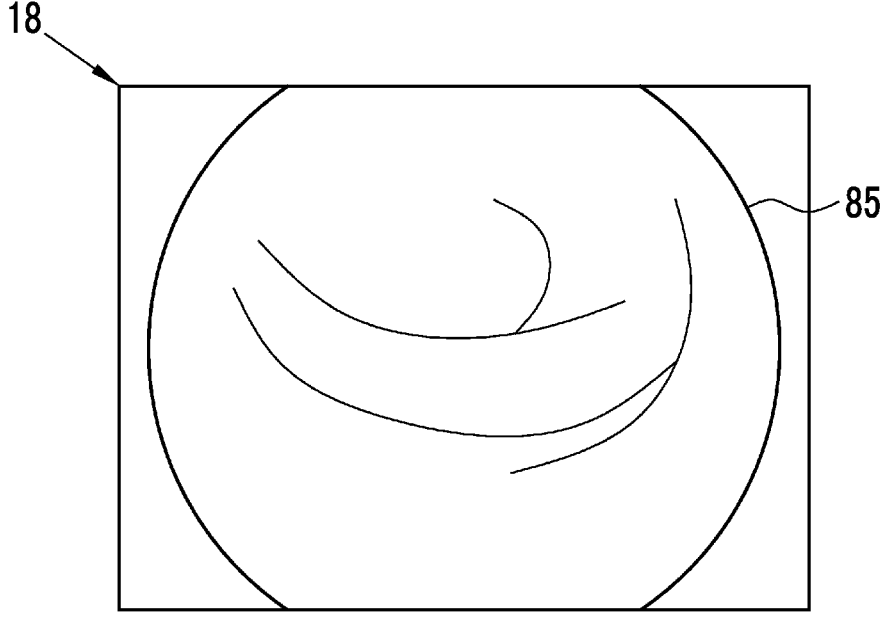
FIG. 14 is an image view of an observation image.

As shown in FIG. 14, in the present embodiment, since a user selects a normal light image to be displayed on the display 18, the display image generation unit 65 performs necessary image processing in order to display the normal light image on the display 18 and uses the normal light image as an observation image 85. Therefore, the normal light image in which an observation target is picked up is continuously displayed on the display. In the present embodiment, a special light image is acquired at a ratio of one frame to six frames, but the special light image is not displayed on the display 18. Instead of displaying one frame of acquired special light image, one frame of normal light image, which is one frame ahead of the acquired special light image, is continuously displayed or the like. Through the setting by the user, the observation image 85 can be switched to the special light image or the like. In this case, the normal light image is acquired at a ratio of one frame to six frames, and the normal light image is not displayed on the display 18.

Figure 15:
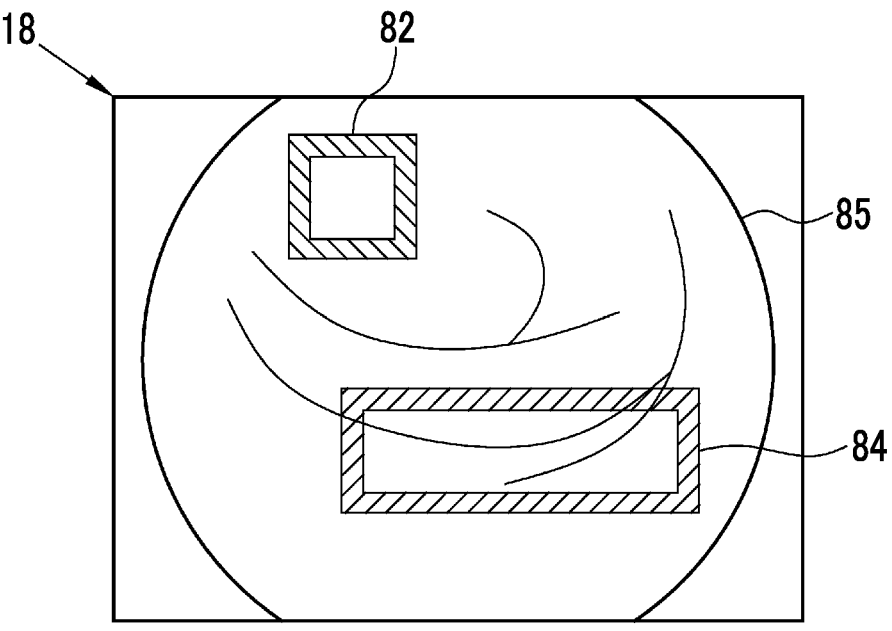
FIG. 15 is an image view for describing a display image, in which figures which are two types of analysis result displays are superimposed on the observation image.

The display control unit 57 performs control of displaying, on the display 18, an analysis result display based on a plurality of analysis results and the observation image 85 based on at least one type of analysis image among a plurality of types of analysis images. Specifically, the display control unit 57 performs control of superimposing a plurality of analysis result displays on the observation image 85 after aligning the positions to form a display image and displaying the display image on the display 18. The plurality of analysis result displays are superimposed on the observation image 85 in a form in which each analysis result display can be distinguished and recognized. In the present embodiment, the FIG. 82 displaying a first analysis result and the FIG. 84 displaying a second analysis result are displayed in colors different from each other. As shown in FIG. 15, the display control unit 57 performs control of superimposing the FIG. 82 displaying the first analysis result and the FIG. 84 displaying the second analysis result on the observation image 85 in different colors.

As described above, in the processor device 16, which is the image analysis processing apparatus, or the endoscope system 10, by performing image analysis for each type of endoscope image, for example, not only image analysis results based on one type of endoscope image selected to be displayed on the display but also image analysis results based on a different type of endoscope image can be quickly obtained. In addition, in a case analysis results obtained well are different depending on the type of endoscope image, even an analysis result which has not been detected in one endoscope image is well detected in the other endoscope image in some cases, and a region-of-interest, such as a lesion, can be prevented from being overlooked.

In the present embodiment, since a normal light image and a special light image are used as analysis images, the normal light image has sufficient brightness, and a lesion is well detected in a distant view through image analysis by the first image analysis unit 71. Even in a case where the special light image has insufficient brightness and the lesion cannot be detected in a distant view through the image analysis by the second image analysis unit 72, the FIG. 82 is superimposed on the observation image 85 and is displayed on the display 18. In particular, in a case where the observation image 85 is mainly observed in a near view as the special light image, a lesion or the like that is darkly displayed on the display 18 in a distant view is displayed as the FIG. 82. Thus, even in a case where the special light image is continuously displayed on the display 18, a region-of-interest, such as a lesion that is difficult to be visually determined and is in a region darkly displayed, can be prevented from being overlooked.

It is preferable that an analysis result includes accuracy related to the analysis result. The accuracy related to the analysis result is a degree to which the analysis result is accurate or a degree to which an error is not included. In a case where the presence or absence of a specific state is used as an analysis result, accuracy indicates a degree to which an error, noise, or the like is included when detecting information of a region in image analysis together with detecting information of a region of the specific state, which is the analysis result. The accuracy related to the analysis result is specifically indicated by a numerical value. For example, in a case where a specific lesion is a cancer, since there can be a type of analysis image through which the cancer can be well detected and a type of analysis image through which the cancer cannot be well detected, depending on the type of analysis image, accuracy related to an analysis result related to detection of the cancer is different. In addition, depending on the situation of analysis image, for example, depending on a state of an image or the like, in which blurring has occurred, accuracy related to an analysis result is different in some cases even in a case where the cancer is detected as an analysis result from the same type of analysis image. Therefore, it is preferable to show the analysis result accuracy in a numerical value according to the situation of each image analysis.

By performing setting such that accuracy related to an analysis result is also displayed as the analysis result through image analysis on a selected analysis image by the image analysis processing unit 63, the accuracy related to the analysis result may be displayed in numerical values and/or text, together with the presence or absence of a lesion and a region in a case where there is a lesion, which are analysis results. In a case of showing the accuracy in a numerical value, it is preferable to show the accuracy through a percentage or the like such that the accuracy increases as the numerical value increases. For example, a case of using a trained model through machine learning in image analysis is preferable since accuracy related an analysis result, which is an analysis result, can be output in numerical values.

Figure 16:
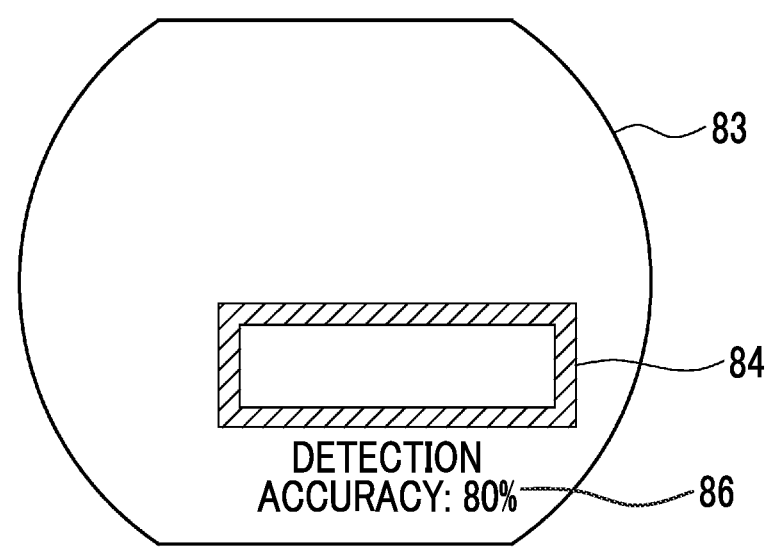
FIG. 16 is an image view for describing a figure and text which are the second analysis result display.

As shown in FIG. 16, in a case where an analysis result includes accuracy related to the analysis result, the second analysis result display 83 includes the FIG. 84 showing a region of a lesion, which is an analysis result, and an accuracy display 86 showing accuracy related to the analysis result when displaying a second analysis result in the present embodiment.

As an analysis result includes accuracy related to the analysis result, details of the analysis result can be learned at a glance. For example, in a case where a region of a lesion is displayed in a figure based on the analysis result, since accuracy related to the analysis result is also displayed, a user can learn diagnostic support information in detail.

Figure 17:
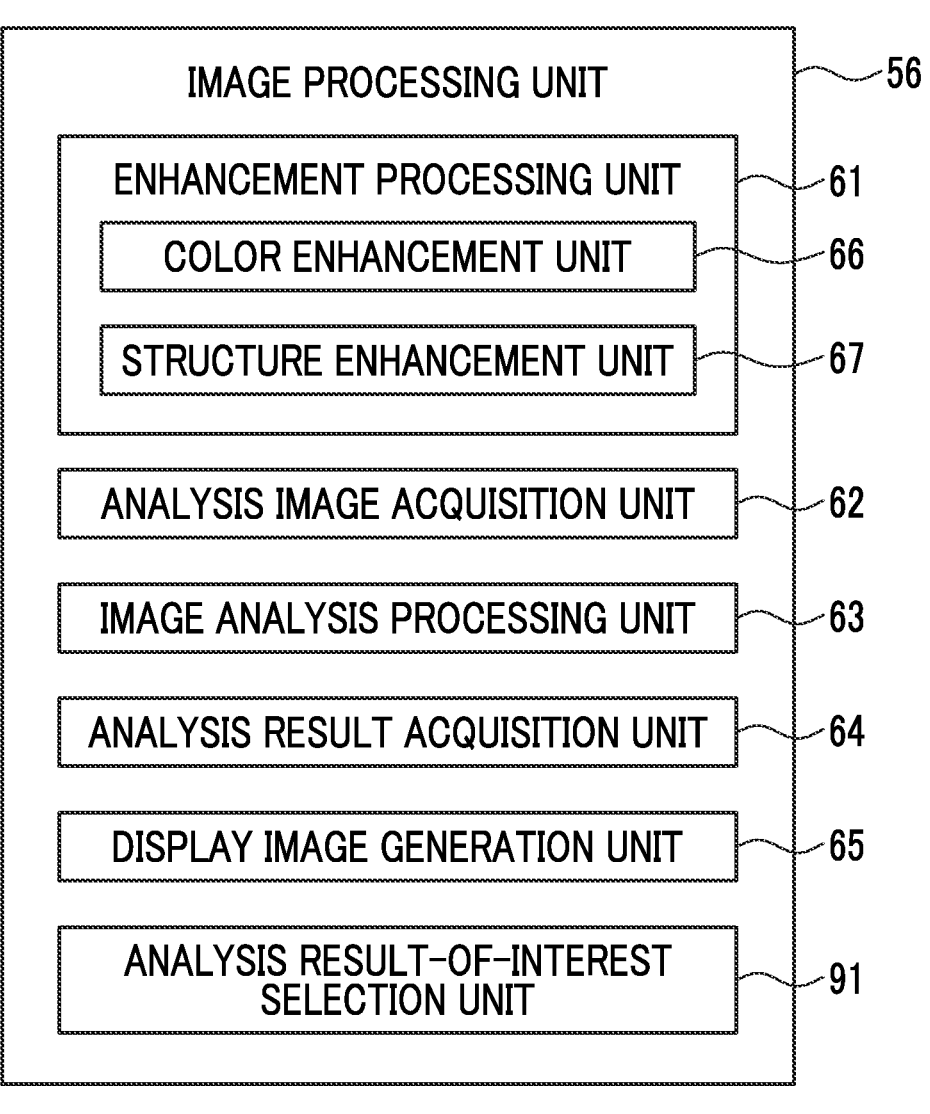
FIG. 17 is a block diagram showing a function of the image processing unit comprising an analysis result-of-interest selection unit.

In addition, an analysis result-of-interest selection unit that selects an analysis result having the highest analysis result accuracy as an analysis result-of-interest by comparing a plurality of analysis results with each other is included, and it is preferable for the display image generation unit 65 to create an analysis result display including the analysis result-of-interest. As shown in FIG. 17, in this case, the image processing unit 56 comprises an analysis result-of-interest selection unit 91.

The analysis result-of-interest selection unit 91 compares a plurality of analysis results with each other. In a case of comparing, when the plurality of analysis results include the same region in an observation target, the analysis results are compared with each other. Then, among the plurality of analysis results, an analysis result having the highest analysis result accuracy included in the analysis results is selected as an analysis result-of-interest. After performing a region determination process on a plurality of analysis images that are sources of the plurality of analysis results in order to determine that the plurality of analysis results include the same region in the observation target, the analysis result-of-interest selection unit 91 may compare the plurality of analysis results with each other.

Figure 18:
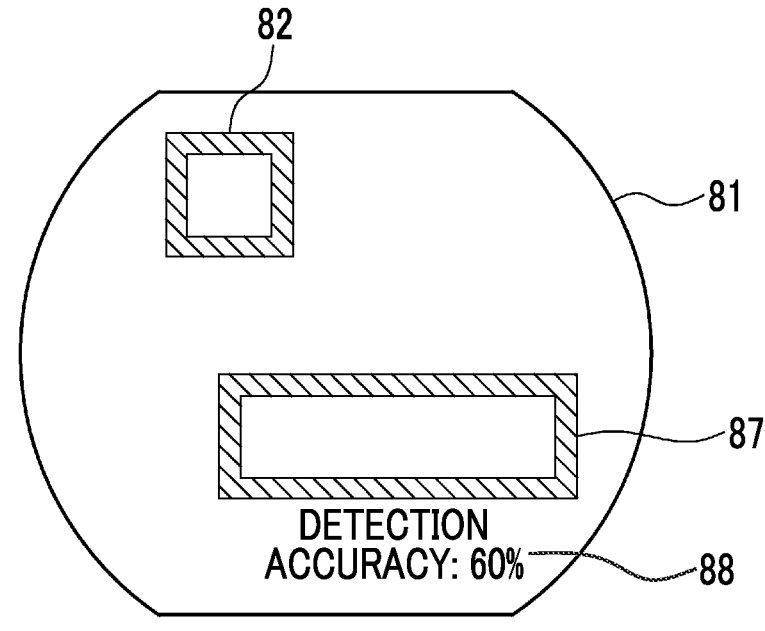
FIG. 18 is an image view for describing a figure or the like showing an analysis result selected by the analysis result-of-interest selection unit.

As shown in FIG. 18, in the present embodiment, in a case where a first analysis result is detected to be a lesion even in the same region as the FIG. 84 showing a second analysis result and the first analysis result display 81 includes a FIG. 87 and an accuracy display 88, the analysis result-of-interest selection unit 91 compares accuracy of the second analysis result shown in the FIG. 84 of 80% (see FIG. 16) and accuracy of the first analysis result shown in the FIG. 87 of 60% with each other. Then, a second analysis result which is an analysis result having high analysis result accuracy is selected as an analysis result-of-interest.

Figure 19:
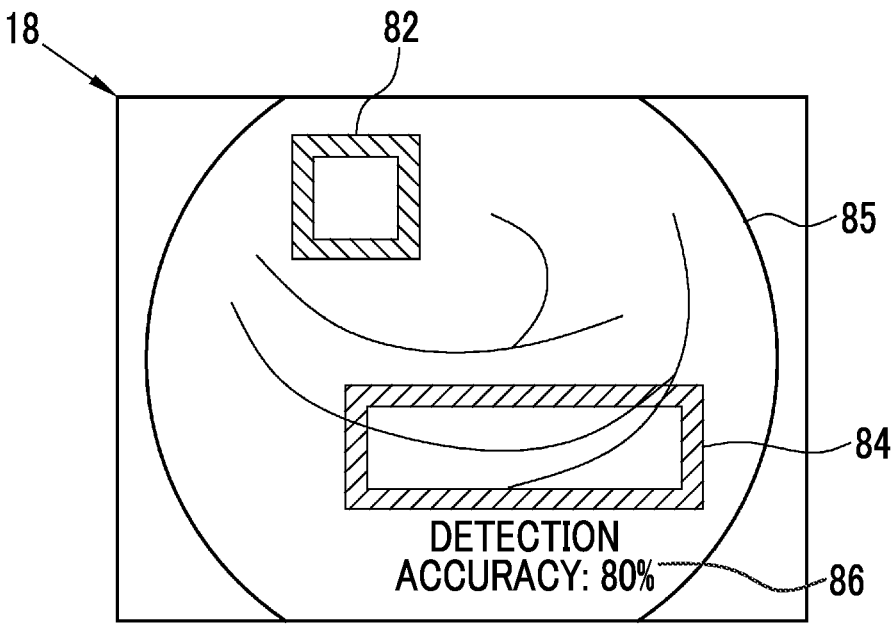
FIG. 19 is an image view for describing a display image in which the figure or the like showing the analysis result selected by the analysis result-of-interest selection unit is superimposed on the observation image.

The analysis result display generation unit 79 (see FIG. 11) creates an analysis result display to include an analysis result-of-interest. As shown in FIG. 19, in the present embodiment, in a case where the analysis result-of-interest selection unit 91 has selected a second analysis result as an analysis result-of-interest, for a lesion in a region shown by the FIG. 84 and the FIG. 87 in an observation target, an analysis result display shown by the FIG. 84 and the accuracy display 86 caused by the second analysis result without showing the FIG. 87 and the accuracy display 88 caused by a first analysis result is generated. The display control unit 57 superimposes the analysis result display on the observation image 85 and displays the analysis result display on the display 18.

With the analysis result-of-interest selection unit 91, analysis results can be displayed with higher accuracy among a plurality of analysis results. Therefore, the accuracy or reliability of image analysis can be improved.

An analysis result may include a probability that a region in an observation target is in a specific state. A probability of being in a specific state is a numerical value indicating the certainty that an observation state is in a specific state set in advance. Specifically, for example, in a case where a specific lesion is a cancer, as it is certain that the specific lesion is a cancer in the observation target, a higher numerical value is displayed as a probability, and as it is not certain that the specific lesion is a cancer while there is a probability of being a cancer, a lower numerical value is displayed as a probability. In particular, in image analysis using a trained model through machine learning, a region, which is a specific state set in advance, in an image and a probability thereof can be output as analysis results. Therefore, by performing setting a method of image analysis on a selected analysis image by an image analysis unit in the image analysis processing unit 63 such that for example, a region of a cancer and a probability thereof are detected, the region of the cancer and the probability thereof are displayed.

Figure 20:
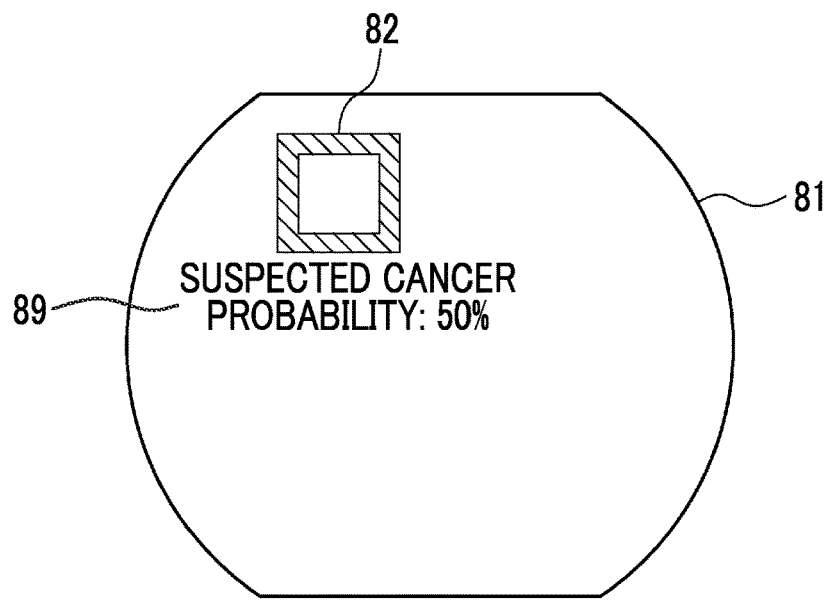
FIG. 20 is an image view for describing a figure and text which are the first analysis result display.

As shown in FIG. 20, in a case where analysis results include a probability that a region in an observation target is in a specific state, the first analysis result display 81 includes the FIG. 82 showing a region of a lesion and a probability display 89 in which the region in the observation target is in a specific state, which are analysis results, when displaying a first analysis result in the present embodiment. In the probability display 89, for example, "a suspected cancer probability of 50%" or the like is shown.

As analysis results include a probability that a region in an observation target is in a specific state, the analysis results can be learned in detail at a glance. For example, in a case where a region of a lesion is displayed in a figure according to the analysis results, since a probability that the region is in a specific state is also displayed, a user can easily learn diagnostic support information in detail, and a lesion or the like can be better prevented from being overlooked.

Figure 21:
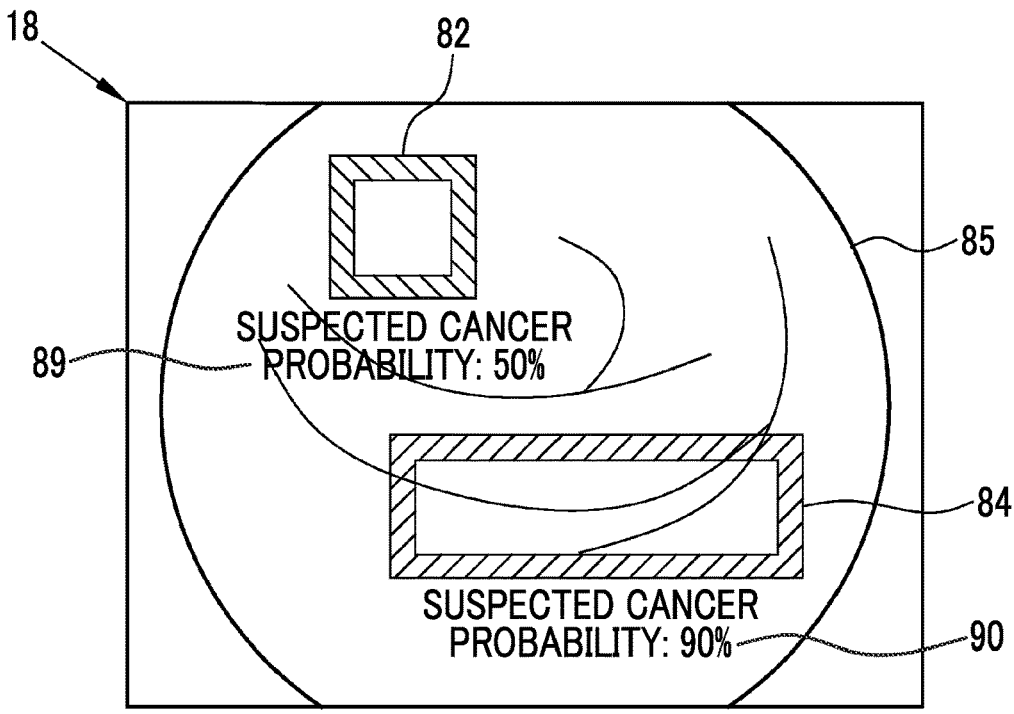
FIG. 21 is an image view for describing a display image, in which a figure and text which are analysis result displays are superimposed on the observation image.

Even a case where an analysis result includes a probability that a region in an observation target is in a specific state can be the same as a case where an analysis result includes accuracy related to the analysis result. For example, in a case where different probabilities are output for the same region of the observation target in a plurality of analysis results, an analysis result display including an analysis result having the highest probability among the probabilities is used. As shown in FIG. 21, in the present embodiment, for a lesion in a region shown by the FIG. 84 or the FIG. 87 (see FIG. 18) in the observation target, an analysis result display shown by the FIG. 84 and a probability display 90 from a second analysis result having the highest probability, without showing the FIG. 87 from a first analysis result and a probability display for a probability that the region in the observation target is in a specific state, which is included in the analysis result, is superimposed on the observation image 85 and is displayed on the display 18. Then, for the region of the FIG. 82 in the first analysis result display 81, since the second analysis result does not include an analysis result of being a lesion, the region of the FIG. 82 shows the FIG. 82 of the first analysis result display 81 and the probability display 89 as they are. As described above, a region of the observation target in which at least one of a plurality of analysis results is a lesion is preferably included an analysis result display and is displayed on a display image.

As analysis results include a probability that a region in an observation target is in a specific state after selecting an analysis result-of-interest from a plurality of analysis results, the accuracy or reliability of image analysis can be further improved, and a region-of-interest, such as a lesion, can be better prevented from being overlooked.

It is preferable for the analysis result acquisition unit 64 to acquire an analysis result in association with the type of analysis image from which the analysis result is obtained, and it is preferable for the display control unit 57 to perform control of displaying, on the display 18, a legend display showing association between an analysis result and the type of analysis image from which the analysis result is obtained. The legend display is a display in an analysis result display and a display showing the type of analysis image in a form of the same color or the like such that the display in the analysis result display is an analysis result of which the type of analysis image can be learned at a glance. Since based on which type of analysis image the analysis result display is obtained can be quickly and easily learned through the legend display, for example, the reliability or the like of the analysis result display can also be learned.

Figure 22:
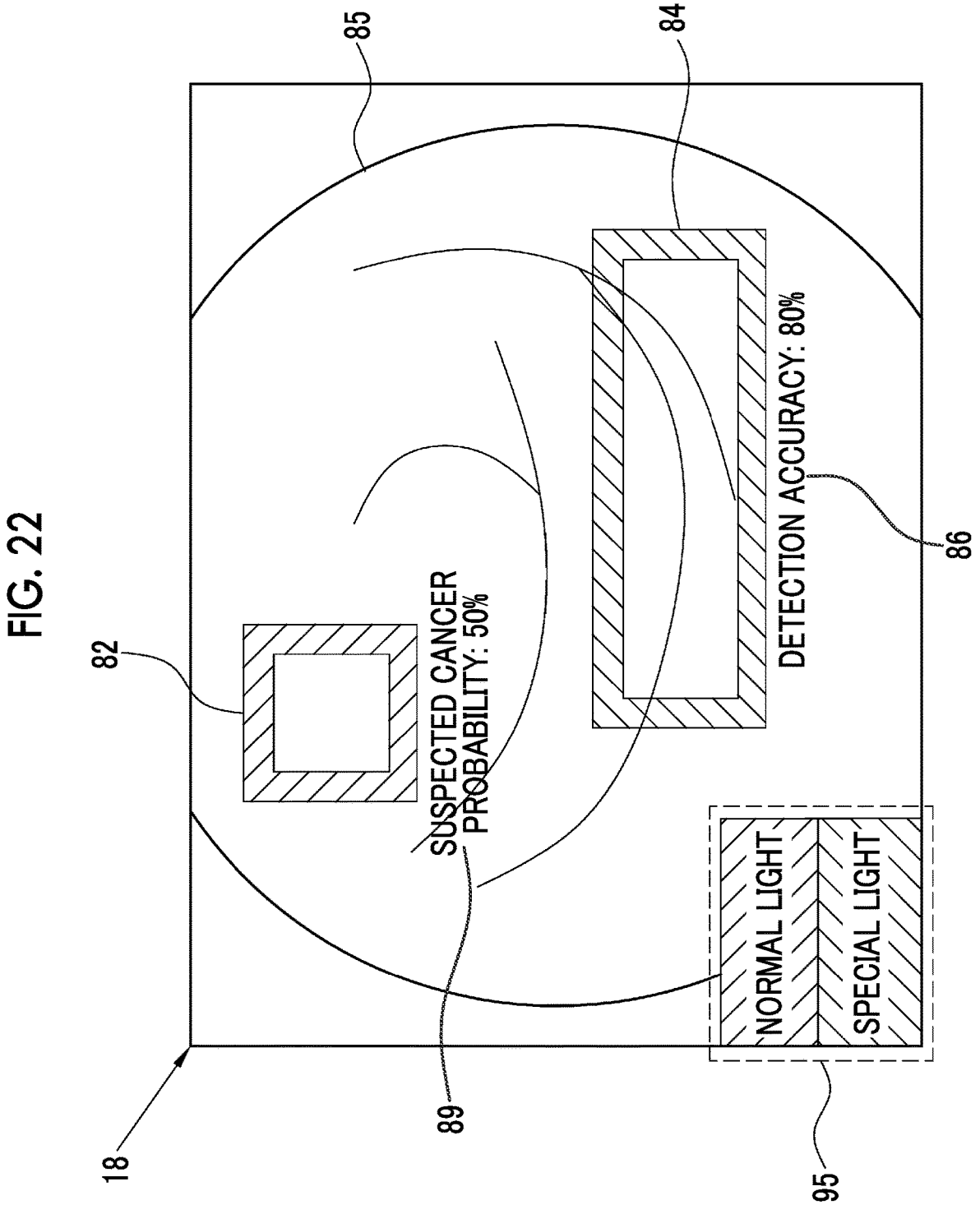
FIG. 22 is an image view for describing a display image comprising a legend display.

As shown in FIG. 22, in the present embodiment, the FIG. 82 showing a first analysis result is an endoscope image obtained using normal light as an analysis image, and the FIG. 84 showing a second analysis result is an endoscope image obtained using special light as an analysis image. Therefore, "normal light" indicating that the endoscope image is obtained with normal light in the same color as the FIG. 82 and "special light" indicating that the endoscope image is obtained with special light in the same color as the FIG. 84 are displayed as a legend display 95 at the lower left of the observation image 85.

In a case where a figure showing an analysis result or the like is displayed by displaying which analysis image the analysis result has been obtained from as a legend, through which image, through which a lesion or the like is well detected, an analysis result has been obtained can be easily learned at a glance. In addition, even in a case where a lesion or the like does not exist in an observation target and no figure showing an analysis result or the like is displayed when a display image is a normal light image, which type of analysis image has been currently acquired, that is, which IEE has been performed can be learned through the legend display 95. For example, illumination light based on which type of special light is used in one period (FIG. 6, 1CY) of illumination light can be learned. Therefore, the legend display 95 is also useful as a display showing which IEE that has been performed at the time point in endoscopy.

Figure 23:
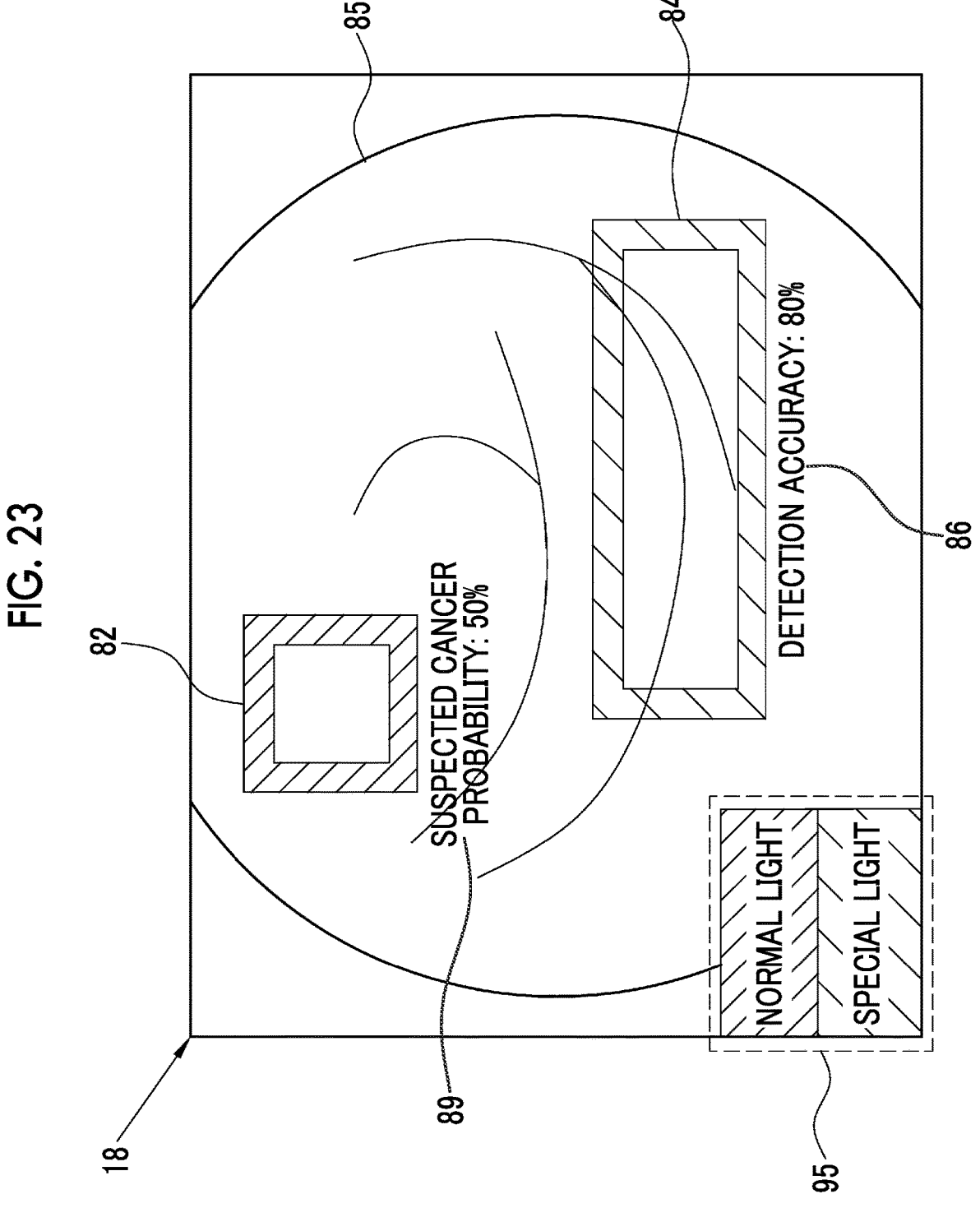
FIG. 23 is an image view for describing a display image inconspicuously displaying an analysis result display based on an image which is not displayed.

In addition, an analysis result based on an analysis image of a type other than the observation image 85 displayed on the display 18 may be an analysis result display distinguished from an analysis result based on an analysis image that is a source of the observation image 85. As shown in FIG. 23, the FIG. 82 and the probability display 89, which are analysis result displays based on a normal light image which is a source of the observation image 85, may be conspicuously shown in a dark color, and the FIG. 84 and the accuracy display 86, which are analysis result displays based on a special light image which is not displayed as in the observation image 85, may be displayed in a light color, a dotted line, or the like so as not to be conspicuous. In FIG. 23, a figure or a display having wide intervals between diagonal lines is shown in a light color or a dotted line.

Figure 24:
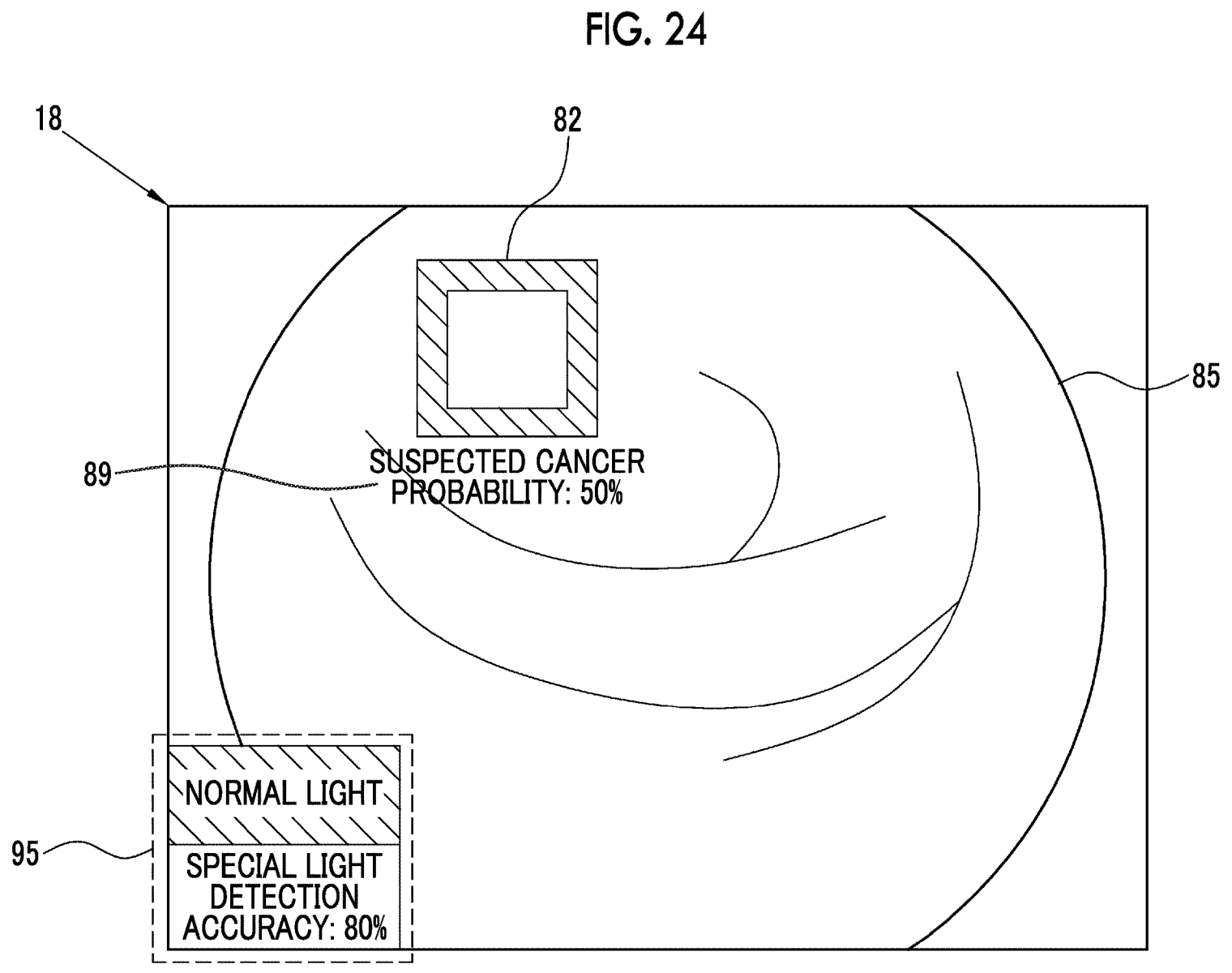

In addition, the FIG. 84 and the accuracy display 86, which are analysis result displays based on a special light image which is not displayed as in the observation image 85, may be shown in a method other than being superimposed on the observation image 85. For example, as shown in FIG. 24, analysis results based on the special light image can be shown in a sentence together with the legend display 95. In addition, the second analysis result display 83 may be shown as a sub-screen outside the observation image 85.

A plurality of types of analysis images may be three or more types without being limited to two types. For example, in an analysis image, an endoscope image obtained by illuminating with normal light is used as a first analysis image, special light caused by the optical spectrum shown in FIG. 5 is used as first special light, an endoscope image obtained by illuminating with the first special light is used as a second type of analysis image, and an endoscope image obtained by illuminating with second special light different from the first special light is used as a third type of analysis image.

Figure 25:
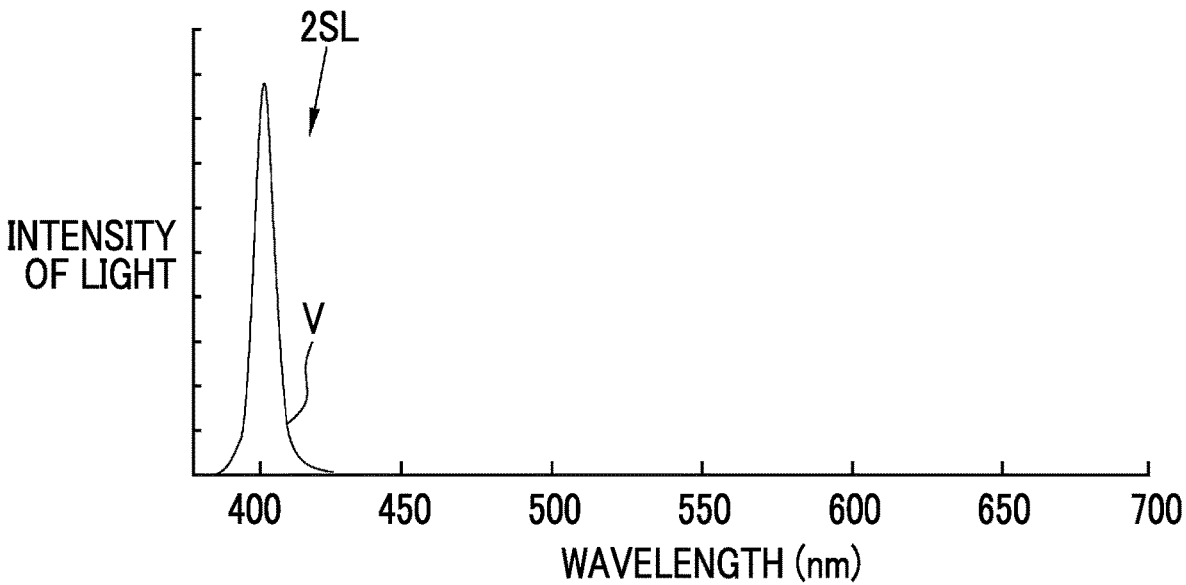
FIG. 25 is a graph showing a spectrum of second special light.

The light source control unit 22 controls each of the LEDs 20a to 20d such that special light having a ratio of intensity of light between the violet light VL, the blue light BL, the green light GL, and the red light RL of Vs2:Bs2:Gs2:Rs2 is emitted as second special light. The ratio of intensity of light of Vs2:Bs2:Gs2:Rs2 corresponds to a light amount condition of second special light. The second special light preferably enhances a superficial blood vessel. For this reason, the second special light emits only the violet light VL which is narrowband light having a small wavelength with a ratio of intensity of light as 1:0:0:0 as shown in FIG. 25.

Figure 26:
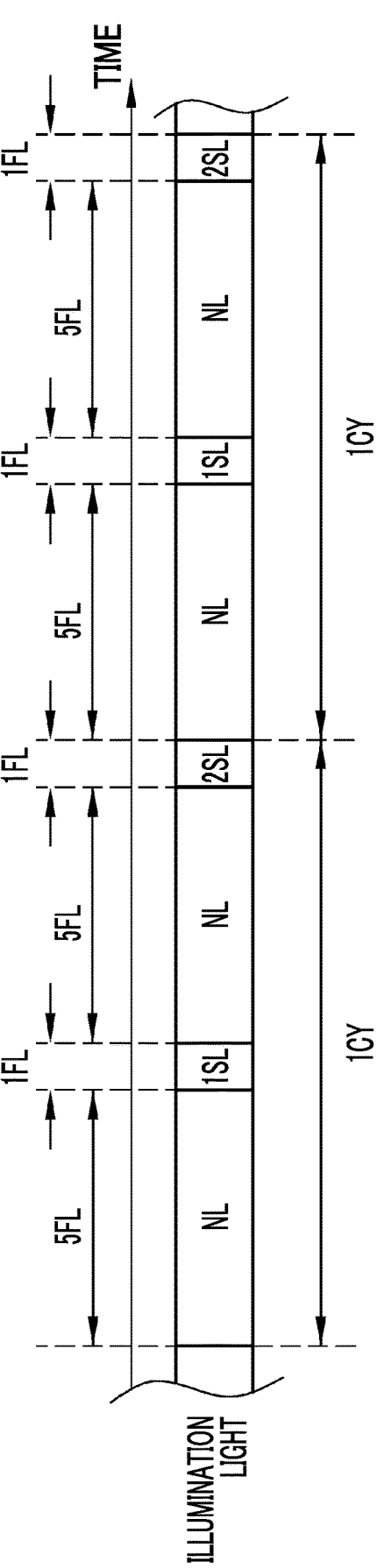
FIG. 26 is an explanatory view for describing an illumination light pattern including the second special light.

In the present embodiment, the light source control unit 22 emits, for example, as shown in FIG. 26, the normal light NL for consecutively five frames (5FL), next, first special light 1SL for one frame (1FL), normal light NL again for consecutively five frames (5FL), and next second special light 2SL for one frame (1FL). With an illumination pattern consisting of this order as one period (1CY), the period is repeated.

Figure 27:
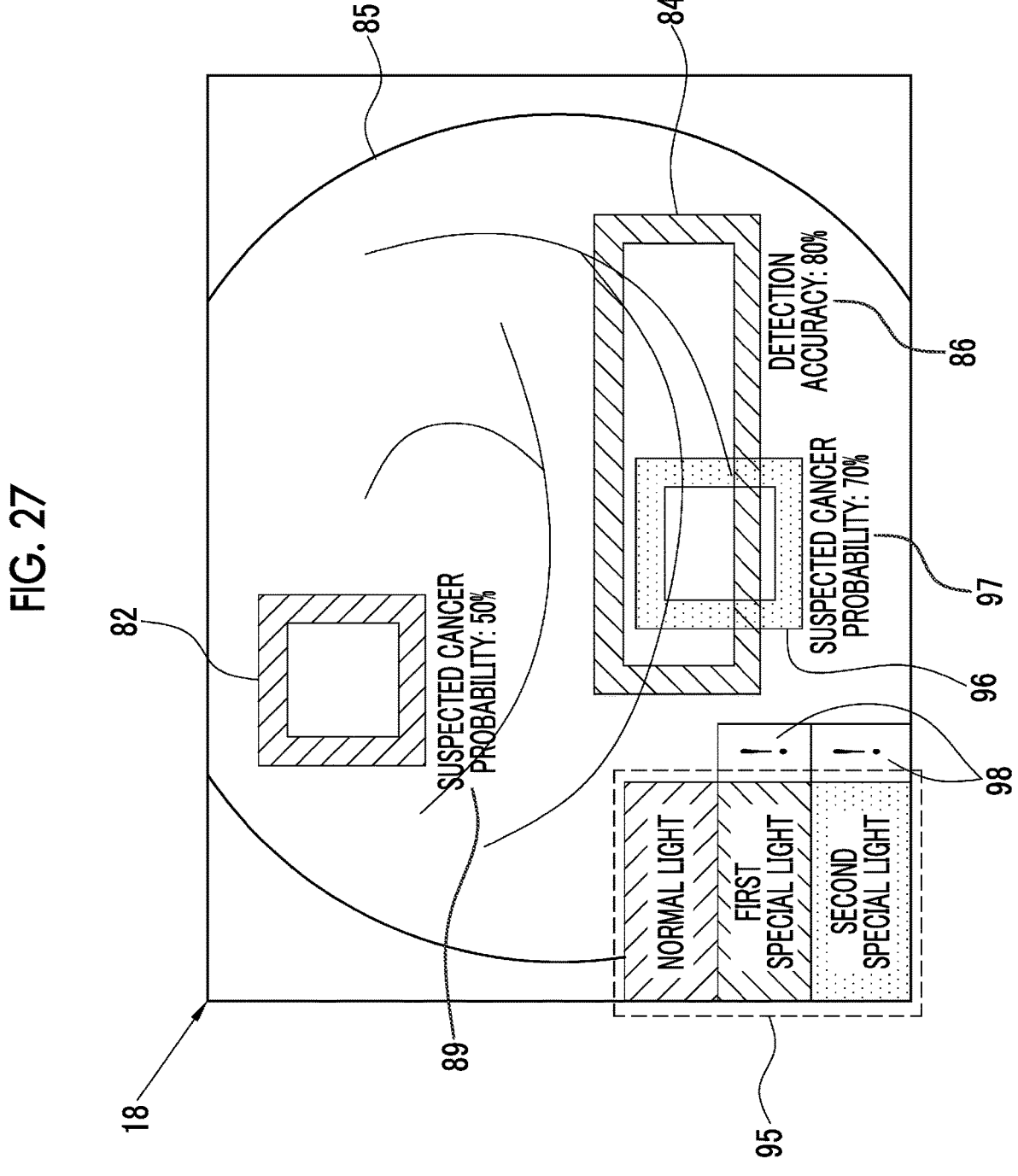
FIG. 27 is an image view for describing a display image in which three types of analysis result displays are superimposed on the observation image.

As in the embodiment, the third image analysis unit 73 (see FIG. 10) performs image analysis on an analysis image based on second special light, and a third analysis result is sent to the analysis result acquisition unit 64. The analysis result acquisition unit 64 acquires a first analysis result of an analysis image based on normal light, a second analysis result of an analysis image based on first special light, and a third analysis result of an analysis image based on second special light. As shown in FIG. 27, the third analysis result is displayed in a FIG. 96.

As shown in FIG. 27, in some cases, the FIG. 96, which is a detection result included in a third analysis result, overlaps the FIG. 84, which is a detection result included in a second analysis result. Since an endoscope image based on first special light shows the structures of a superficial blood vessel, a polyp, and the like well and an endoscope image based on second special light shows an enhanced superficial blood vessel, a region where a region of the FIG. 84 included in a second analysis result and a region of the FIG. 96 included in a third analysis result overlap each other is a region having a high probability that there is an abnormality in the structure of the superficial blood vessel or the like, and an alert display 98 that particularly calls attention of a user is included as an analysis result.

In addition, in the image analysis processing unit 63, in a case where analysis results of a plurality of specific analysis images include the same region, the analysis results with respect to the region may include an observation target being in a specific state. As in the present embodiment, in a case where a second analysis result and a third analysis result include the same region, the analysis results may be different from a case where a specific region is included in only the second analysis result or only the third analysis result. In a case where each of the second analysis result and the third analysis result includes a probability of a specific lesion as a different analysis result, both of the second analysis result and the third analysis result include a region displaying a depth direction of the specific lesion or the like. For example, by combining being able to detect even in a case where the specific lesion such as a cancer is mild, accurately showing a region of the specific lesion in the depth direction or the like, or the like through image analysis using machine learning, analysis results with better accuracy can be included.

Figure 28:
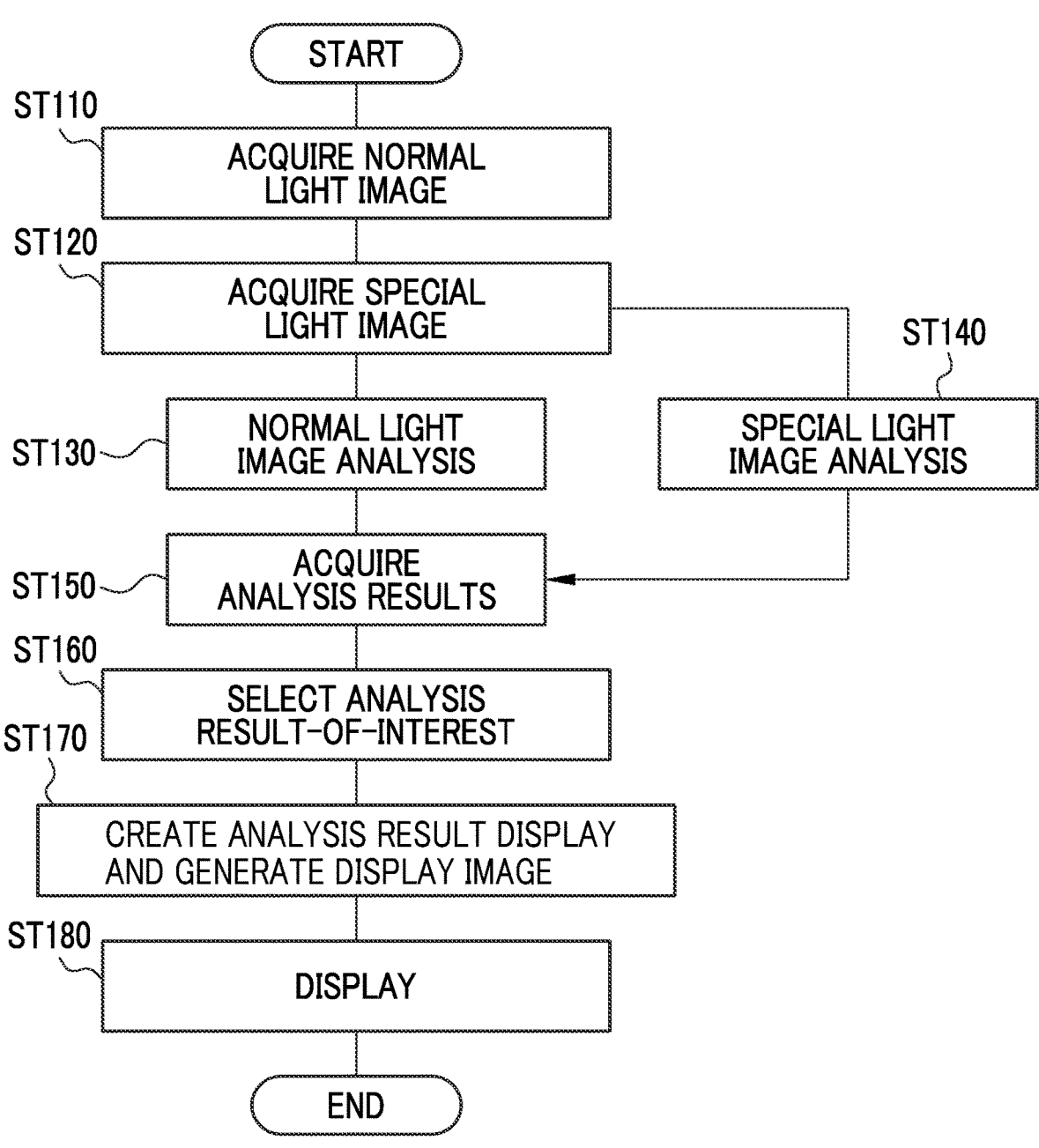
FIG. 28 is a flow chart describing a flow of processes of an image analysis processing apparatus.

Next, the series of flows of processes related to image analysis performed by the processor device 16, which is the image analysis processing apparatus, or the endoscope system 10 will be described with reference to a flowchart shown in FIG. 28. In a case where observation starts, illumination light is emitted in order set in advance in accordance with a predetermined illumination light pattern (see FIG. 6). First, illumination light is normal light, and a normal light image is acquired (Step ST110). Next, illumination light is special light, and a special light image is acquired (Step ST120). Normal light image analysis (Step ST130) and special light image analysis (Step ST140) are performed in parallel. A first analysis result caused by the normal light image analysis and a second analysis result caused by the special light image analysis are acquired by the analysis result acquisition unit (Step ST150). In a case where a plurality of analysis results include an analysis result of an observation target with respect to the same region, the analysis result-of-interest selection unit selects an analysis result-of-interest (Step ST160). An analysis result display is generated in accordance with the selected analysis result-of-interest, and as set in advance, a display image based on one type of a plurality of analysis images is generated (Step ST170). The display control unit 57 displays the analysis result display and the display image on the display 18 (Step ST180).

Figure 29:
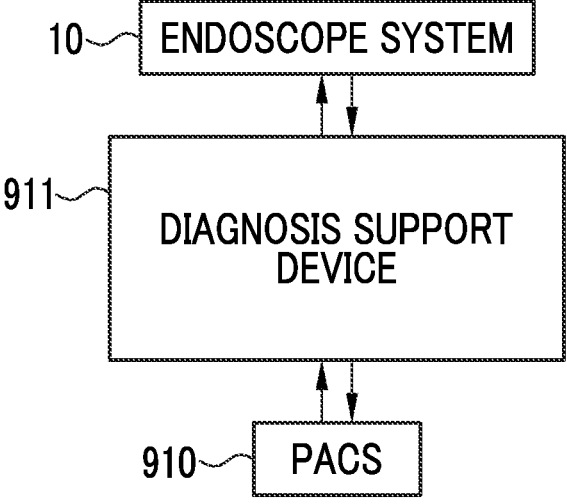
FIG. 29 is an explanatory view showing a diagnosis support device.
Figure 30:
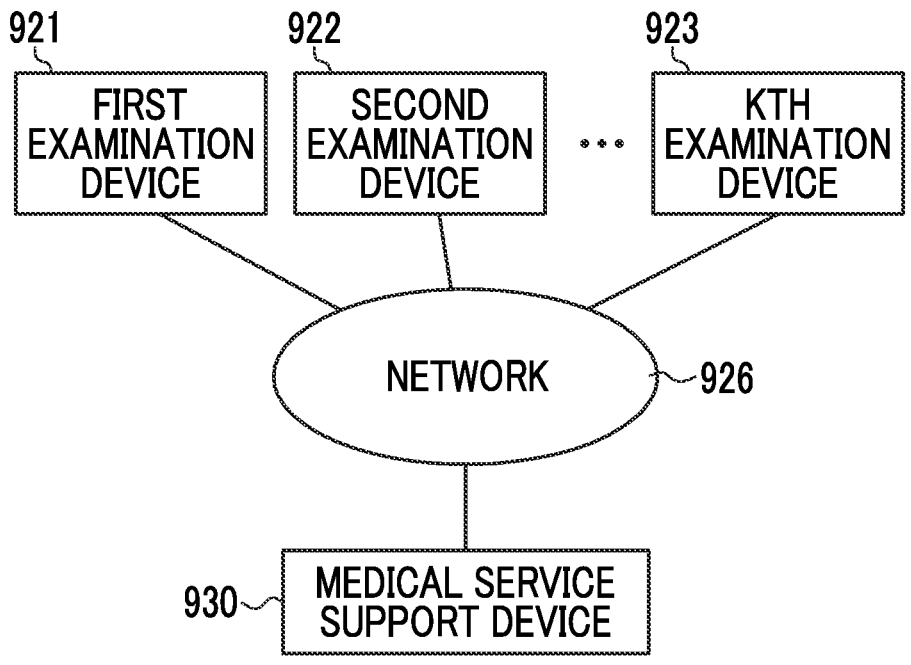
FIG. 30 is an explanatory view showing a medical service support device.

Although the processor device 16 functions as the image analysis processing apparatus in the embodiment, a modification example, and the like, the image analysis processing apparatus including the image processing unit 56 may be provided separately from the processor device 16. In addition, as shown in FIG. 29, the image processing unit 56 can be provided at a diagnosis support device 911 that acquires an RAW image captured by the endoscope 12, for example, directly from the endoscope system 10 or indirectly from picture archiving and communication systems (PACS) 910. In addition, as shown in FIG. 30, the image processing unit 56 can be provided at a medical service support device 930 that is connected to various types of examination devices including a first examination device 921, a second examination device 922, . . . , and a Kth examination device 923, including the endoscope system 10, via a network 926.

Each of the embodiments and the modification examples can be performed in any combination of some or all of the embodiments and the modification examples. In addition, although the endoscope 12 uses a so-called soft endoscope having the flexible insertion part 12a in each of the embodiments and the modification examples, the present invention is suitable also in a case of using a capsule-type endoscope used by swallowing an observation target or a hard endoscope (laparoscope) using a surgical operation or the like.

The embodiment, the modification example, and the like include an operation method of an image analysis processing apparatus that comprises a processor and performs image analysis based on an image obtained by picking up an image of an observation target using an endoscope, the operation method of an image analysis processing apparatus comprising an analysis image acquisition step of acquiring a plurality of types of analysis images used in image analysis, an image analysis processing step of performing image analysis on an analysis image in parallel for each type of analysis image, an analysis result acquisition step of acquiring a plurality of analysis results through image analysis, and a display control step of performing control of displaying, on a display, a display image including an analysis result display based on the plurality of analysis results and at least one type of analysis image among the plurality of types of analysis images.

In addition, the embodiment, the modification example, and the like include a program for an image analysis processing apparatus installed in an image analysis processing apparatus that comprises a processor and performs image analysis based on an image of an observation target using an endoscope, the program for an image analysis processing apparatus for causing a computer to realize an analysis image acquisition function of acquiring a plurality of types of analysis images used in image analysis, an image analysis processing function of performing image analysis on an analysis image in parallel for each type of analysis image, an analysis result acquisition function of acquiring a plurality of analysis results through image analysis, and a display control function of performing control of displaying, on a display, a display image including an analysis result display based on the plurality of analysis results and at least one type of analysis image among the plurality of types of analysis images.

In the embodiment, hardware structures of processing units that perform various types of processes, including the control unit 51, the image acquisition unit 52, the DSP 53, the noise-reduction section 54, the conversion unit 55, the image processing unit 56, and the display control unit 57 included in the processor device 16, which is the image analysis processing apparatus, are various types of processors shown below. The various types of processors include a central processing unit (CPU) that is a general-purpose processor functioning as various types of processing units, which execute software (program) and function as various types of processing units, a programmable logic device (PLD) that is a processor which can change a circuit configuration after manufacturing, such as a field programmable gate array (FPGA), and a dedicated electric circuit that is a processor which has a circuit configuration exclusively designed for executing various types of processes.

One processing unit may be composed of one of the various types of processors or may be composed of the same type or different types of two or more processors (for example, a plurality of FPGAs or a combination of the CPU and the FPGA). In addition, one processor may configure a plurality of processing units. As an example of configuring a plurality of processing units with one processor, first, there is a form in which one processor is configured by a combination of one or more CPUs and software and the processor functions as the plurality of processing units, as represented by a computer such as a client and a server. Second, there is a form in which a processor that realizes functions of the entire system including a plurality of processing units with one integrated circuit (IC) chip is used, as represented by a system on chip (SoC) or the like.

As described above, the various types of processing units are composed of one or more of the various types of processors used as a hardware structure.

Further, the hardware structures of the various types of processors are, more specifically, an electric circuit (circuitry) in a form in which circuit elements such as semiconductor elements are combined.

The present invention can be useful also in a system, a device, or the like that acquires a medical image (including a motion picture) other than an endoscope image, in addition to an endoscope system that acquires an endoscope image or the like, a processor device, other related devices, and the like. For example, the present invention can be applied to an ultrasonic examination device, an X-ray image imaging device (including a computed tomography (CT) examination device and a mammography device), a magnetic resonance imaging (MRI) device, and the like.

EXPLANATION OF REFERENCES

10: endoscope system
12: endoscope

12*a*: insertion part
12*b*: operating part
12*c*: bendable part
12*d*: distal end part
12*e*: angle knob
12*f*: treatment tool insertion port
12*g*: scope button
13: zoom operation part
14: light source device
16: processor device
18: display
19: keyboard
20: light source unit
20*a*: V-LED
20*b*: B-LED
20*c*: G-LED
20*d*: R-LED
22: light source control unit
30*a*: illumination optical system
30*b*: imaging optical system
41: light guide
42: illumination lens
43: objective lens
44: zoom lens
45: image sensor
51: control unit
52: image acquisition unit
53: DSP
54: noise-reduction section
55: conversion unit
56: image processing unit
57: display control unit
61: enhancement processing unit
62: analysis image acquisition unit
63: image analysis processing unit
64: analysis result acquisition unit
65: display image generation unit
66: color enhancement unit
67: structure enhancement unit
71: first image analysis unit
72: second image analysis unit
73: third image analysis unit
74: nth image analysis unit
75: first association information acquisition unit
76: second association information acquisition unit
77: third association information acquisition unit
78: nth association information acquisition unit
79: analysis result display generation unit
80: observation image generation unit
81: first analysis result display
82, 84, 87, 96: FIG.
83: second analysis result display
85: observation image
86, 88: accuracy display
89, 97: probability display
91: analysis result-of-interest selection unit
95: legend display
98: alert display
910: PACS
911: diagnosis support device
921: first examination device
922: second examination device
923: Kth examination device
926: network
930: medical service support device
NL: normal light
SL: special light 1SL: first special light
2SL: second special light
ST110 to ST180: Step
What is claimed is:

1. An image analysis processing apparatus that performs image analysis based on an image obtained by picking up an image of an observation target using an endoscope, the image analysis processing apparatus comprising:
a processor,
wherein the processor is configured to:
acquire, as a plurality of mutually different types of analysis images used in image analysis, images respectively obtained by picking up the observation target under normal light, first special light, and second special light whose optical spectra differ from one another;
perform the image analysis of the analysis image in parallel for each type of the analysis image;
acquire a plurality of analysis results through the image analysis; and
perform control of displaying, on a display, an analysis result display based on the plurality of analysis results and a display image based on at least one type of the analysis image among the plurality of types of analysis images, and
wherein, in a case where the analysis result obtained under the first special light and the analysis result obtained under the second special light include an overlapped region, the processor is further configured to obtain, and cause the display to display, another analysis result that indicates a specific state of the observation target different from each of the analysis results.

2. The image analysis processing apparatus according to claim 1,
wherein the processor is configured to perform the image analysis independently for each type of the analysis image.

3. The image analysis processing apparatus according to claim 1,
wherein the processor is configured to:
acquire association information in which a specific state of the observation target and the analysis image obtained by picking up an image of the observation target including the specific state are associated with each other in advance; and
obtain the analysis result based on the analysis image and the association information.

4. The image analysis processing apparatus according to claim 3,
wherein the processor is configured to:
acquire the association information for each type of the analysis image; and
obtain the analysis result based on the analysis image and the association information acquired corresponding to the type of the analysis image.

5. The image analysis processing apparatus according to claim 3,
wherein the specific state is at least one of a state where a structure of the observation target is abnormal, a state where the observation target is a specific lesion, or a state where a value of biological information of the observation target is abnormal.

6. The image analysis processing apparatus according to claim 3,
wherein the analysis result includes information of a region of the specific state of the observation target.

7. The image analysis processing apparatus according to claim 1,
wherein the analysis result includes accuracy related to the analysis result.

8. The image analysis processing apparatus according to claim 7,
wherein the processor is configured to:
select the analysis result having highest accuracy related to the analysis result as an analysis result-of-interest by comparing the plurality of analysis results with each other; and
create the analysis result display including the analysis result-of-interest.

9. The image analysis processing apparatus according to claim 1,
wherein the processor is configured to:
generate a first analysis image by performing an enhancement process on the image; and
acquire the first analysis image as one type of the analysis image.

10. The image analysis processing apparatus according to claim 9,
wherein the processor is configured to perform a color enhancement process or a structure enhancement process on the image.

11. The image analysis processing apparatus according to claim 1,
wherein the processor is configured to:
acquire the analysis result in association with the type of the analysis image from which the analysis result is obtained; and
perform control of displaying, on the display, a legend display showing association between the analysis result and the type of the analysis image from which the analysis result is obtained.

12. An endoscope system comprising:
the image analysis processing apparatus according to claim 1; and
a light source that emits illumination light with which the observation target is irradiated.

13. The endoscope system according to claim 12,
wherein the processor is configured to acquire the image obtained by picking up an image of the observation target illuminated with each of a plurality of rays of illumination light emitted by the light source, which have optical spectra different from each other, as each of different types of the analysis images from each other.

14. The endoscope system according to claim 13,
wherein the processor is configured to acquire the image obtained by picking up an image of the observation target illuminated with white illumination light emitted by the light source as one type of the analysis image.

15. The endoscope system according to claim 13,
wherein the processor is configured to acquire the image obtained by picking up an image of the observation target illuminated with illumination light, which is emitted by the light source and includes narrowband light in a wavelength range set in advance, as one type of the analysis image.

16. The endoscope system according to claim 12,
wherein the light source repeatedly emits each of a plurality of rays of illumination light having optical spectra different from each other in order set in advance.

17. The endoscope system according to claim 12,
wherein the processor is configured to:

acquire the analysis result in association with the type of the analysis image from which the analysis result is obtained; and perform control of displaying, on the display, a legend display showing association between the analysis result and the type of the analysis image from which the analysis result is obtained.

18. The image analysis processing apparatus according to claim 1, wherein, in a case where the analysis result obtained under the normal light and the analysis result obtained under at least one special light include an overlapped region, the processor is further configured to select one of the analysis results as an analysis result-of-interest.

19. An operation method of an image analysis processing apparatus that performs image analysis based on an image obtained by picking up an image of an observation target using an endoscope, the operation method comprising:

an analysis image acquisition step of acquiring, as a plurality of mutually different types of analysis images used in image analysis, images respectively obtained by picking up the observation target under normal light, first special light, and second special light whose optical spectra differ from one another;

an image analysis processing step of performing the image analysis on the analysis image in parallel for each type of the analysis image;

an analysis result acquisition step of acquiring a plurality of analysis results through the image analysis; and a display control step of performing control of displaying, on a display, a display image including an analysis result display based on the plurality of analysis results and at least one type of the analysis image among the plurality of types of analysis images, wherein the operation method further comprises, in a case where the analysis result obtained under the first special light and the analysis result obtained under the second special light include an overlapped region, obtaining, and causing the display to display, another analysis result that indicates a specific state of the observation target different from each of the analysis results.

20. A non-transitory computer readable medium for storing a computer-executable program for performing image analysis based on an image obtained by picking up an image of an observation target using an endoscope, the computer-executable program causing a computer to execute:

an analysis image acquisition function of acquiring, as a plurality of mutually different types of analysis images used in image analysis, images respectively obtained by picking up the observation target under normal light, first special light, and second special light whose optical spectra differ from one another;

an image analysis processing function of performing the image analysis on the analysis image in parallel for each type of the analysis image;

an analysis result acquisition function of acquiring a plurality of analysis results through the image analysis; and a display control function of performing control of displaying, on a display, a display image including an analysis result display based on the plurality of analysis results and at least one type of the analysis image among the plurality of types of analysis images, wherein the computer-executable program further causes the computer to execute, in a case where the analysis result obtained under the first special light and the analysis result obtained under the second special light include an overlapped region, obtaining, and causing the display to display, another analysis result that indicates a specific state of the observation target different from each of the analysis results.

* * * * *